(12) United States Patent
Rosenzweig et al.

(10) Patent No.: US 9,896,700 B2
(45) Date of Patent: Feb. 20, 2018

(54) ENGINEERED RECOMBINANT ENZYMES FOR METHANE OXIDATION

(71) Applicants: Northwestern University, Evanston, IL (US); California Institute of Technology, Pasadena, CA (US); Protabit LLC, Pasadena, CA (US)

(72) Inventors: Amy C Rosenzweig, Winnetka, IL (US); Thomas J. Lawton, Chicago, IL (US); Alex Nisthal, Pasadena, CA (US); Jan S. Kostecki, Pasadena, CA (US); Heidi K. Privett, Pasadena, CA (US); Frederick Lee, Pasadena, CA (US); Barry Olafson, Pasadena, CA (US); Athanasios D. Dousis, Pasadena, CA (US)

(73) Assignees: NORTHWESTERN UNIVERSITY, Evanston, IL (US); PROTABIT, LLC, Pasadena, CA (US); CALIFORNIA INSTITUTE OF TECHNOLOGY, Pasadena, CA (US)

(*) Notice: Subject to any disclaimer, the term of this patent is extended or adjusted under 35 U.S.C. 154(b) by 0 days.

(21) Appl. No.: 15/065,266

(22) Filed: Mar. 9, 2016

(65) Prior Publication Data
US 2016/0265003 A1 Sep. 15, 2016

Related U.S. Application Data

(60) Provisional application No. 62/130,290, filed on Mar. 9, 2015.

(51) Int. Cl.
*C12P 7/04* (2006.01)
*C12N 9/02* (2006.01)
*C12N 1/20* (2006.01)
*C12N 11/00* (2006.01)
*C12M 1/40* (2006.01)
(Continued)

(52) U.S. Cl.
CPC .................. *C12P 7/04* (2013.01); *C10L 1/02* (2013.01); *C12M 21/12* (2013.01); *C12M 21/18* (2013.01); *C12N 9/0073* (2013.01); *C12N 11/00* (2013.01); *C10L 2200/0254* (2013.01); *C10L 2200/0469* (2013.01); *C10L 2290/26* (2013.01); *C12Y 114/13025* (2013.01)

(58) Field of Classification Search
None
See application file for complete search history.

(56) References Cited

U.S. PATENT DOCUMENTS

| | | | |
|---|---|---|---|
| 2003/0134352 A1* | 7/2003 | Freimuth | C12P 21/02 435/69.1 |
| 2007/0037246 A1* | 2/2007 | Butt | C07K 14/00 435/69.1 |

OTHER PUBLICATIONS

Hernandez et al., "Control of protein immobilization: Coupling immobilization and site-directed mutagenesis to improve biocatalyst or biosensor performance", Enzyme and Microbial Technology, vol. 48, pp. 107-122, 2011.*

(Continued)

*Primary Examiner* — Richard Ekstrom
(74) *Attorney, Agent, or Firm* — Casimir Jones SC; David Staple

(57) ABSTRACT

Provided herein are soluble engineered polypeptides for oxidizing hydrocarbons, and methods of use, manufacture, and design thereof. In particular, soluble, polypeptides capable of oxidizing methane to methanol (e.g., hydroxylation) are provided.

10 Claims, 9 Drawing Sheets

(51) Int. Cl.
 C12M 1/00 (2006.01)
 C10L 1/02 (2006.01)

(56) References Cited

OTHER PUBLICATIONS

Balasubramanian et al., Oxidation of methane by a biological dicopper centre. Nature. May 6, 2016;465(7294):115-9.
Bao et al., Highly efficient expression and purification system of small-size protein domains in *Escherichia coli* for biochemical characterization. Protein Expr Purif. Jun. 2006;47(2):599-606.
Cabantous et al., In vivo and in vitro protein solubility assays using split GFP. Nat Methods. Oct. 2006;3(10):845-54.
Canutescu et al., Cyclic coordinate descent: A robotics algorithm for protein loop closure. Protein Sci. May 2003;12(5):963-72.
Chennamsetty et al., Prediction of Aggregation Prone Regions of Therapeutic Proteins. J Phys Chem B. May 2010;114(19):6614-24.
Chica et al., Generation of longer emission wavelength red fluorescent proteins using computationally designed libraries. Proc Natl Acad Sci U S A. Nov. 23, 2010;107(47):20257-62.
Conrado et al., Chemistry. Envisioning the bioconversion of methane to liquid fuels. Science. Feb. 7, 2014;343(6171):621-3.
Correa et al., Tuning different expression parameters to achieve soluble recombinant proteins in *E. coli*: advantages of high-throughput screening. Biotechnol J. Jun. 2011;6(6):715-30.
Feldhaus et al., Flow-cytometric isolation of human antibodies from a nonimmune *Saccharomyces cerevisiae* surface display library. Nat Biotechnol. Feb. 2003;21(2):163-70.
Garcia-Fruitos et al., Aggregation as bacterial inclusion bodies does not imply inactivation of enzymes and fluorescent proteins. Microb Cell Fact. Sep. 12, 2005;4:27.
Gastinel et al., Expression and crystallization of a soluble and functional form of an Fc receptor related to class I histocompatibility molecules. Proc Natl Acad Sci U S A. Jan. 15, 1992;89(2):638-42.
Gibson et al., Enzymatic assembly of DNA molecules up to several hundred kilobases. Nat Methods. May 2009;6(5):343-5.
Guerois et al., Predicting changes in the stability of proteins and protein complexes: A study of more than 1000 mutations. J Mol Biol. Jul. 5, 2002;320(2):369-87.
Haynes et al., Rethinking biological activation of methane and conversion to liquid fuels. Nat Chem Biol. May 2014;10(5):331-9.
Kjellstrom et al., Public health impact of global heating due to climate change: potential effects on chronic non-communicable diseases. Int J Public Health. Apr. 2010;55(2):97-103.
Lee et al., An episomal expression vector for screening mutant gene libraries in Pichia pastoris. Plasmid. Jul. 2005;54(1):80-5.
Lieberman et al., Crystal structure of a membrane-bound metalloenzyme that catalyses the biological oxidation of methane. Nature. Mar. 10, 2005;434(7030):177-82.
Phillips et al., The combined use of the Thermofluor assay and ThermoQ analytical software for the determination of protein stability and buffer optimization as an aid in protein crystallization. Curr Protoc Mol Biol. Apr. 2011;Chapter 10:Unit10.28.
Rohl et al., Protein structure prediction using rosetta. Methods Enzymol. 2004;383:66-93.
Skerra et al.,Use of the Strep-tag and streptavidin for detection and purification of recombinant proteins. Methods Enzymol. 2000;326:271-304.
Smith et al., Crystal structure and characterization of particulate methane monooxygenase from Methylocystis species strain M.Biochemistry. Nov. 29, 2011;50(47):10231-40.
Taylor et al., Discrimination of thermophilic and mesophilic proteins. BMC Struct Biol. May 17, 2010;10 Suppl 1:S5.
Tinberg et al., Dioxygen activation in soluble methane monooxygenase. Acc Chem Res. Apr. 19, 2011;44(4):280-8.
Trotsenko et al., Metabolic aspects of aerobic obligate methanotrophy. Adv Appl Microbiol. 2008;63:183-229.
Unger et al., Applications of the Restriction Free (RF) cloning procedure for molecular manipulations and protein expression. J Struct Biol. Oct. 2010;172(1):34-44.
Zahn et al., Membrane-associated methane monooxygenase from Methylococcus capsulatus (Bath) J Bacteriol. Feb. 1996;178(4):1018-29.

\* cited by examiner

ENGINEERED RECOMBINANT ENZYMES FOR METHANE OXIDATION

This invention was made with government support under grant number GM070473 AND awarded by the National Institutes of Health and 1346523 (STTR Grant) awarded by the National Science Foundation. The government has certain rights in the invention.

FIELD

Provided herein are soluble engineered polypeptides for oxidizing hydrocarbons, and methods of use, manufacture, and design thereof. In particular, soluble, polypeptides capable of oxidizing methane to methanol (e.g., hydroxylation) are provided.

BACKGROUND

Methane, the primary component of natural gas, is a cheap and abundant feedstock that is costly to transport and requires significant capital expenditures to convert to higher value products (refs. 1, 2; incorporated by reference in their entireties). As a result, natural gas produced in remote locations such as the Bakken Shale is flared, leading to over $18 billion worth of methane being wasted per year (ref 3; incorporated by reference in its entirety). One potential solution is to use biological systems for methane conversion. These systems are predicted to require lower capital expenditures per barrel than traditional gas-to-liquid Technology (refs. 1, 2; incorporated by reference in their entireties).

In nature, methane is aerobically oxidized by bacteria known as methanotrophs, which utilize it for energy production and carbon fixation (ref. 4; incorporated by reference in its entirety). Methane enters the methanotroph metabolic pathway by the action of methane monooxygenases (MMOs), which oxidize methane to methanol (ref. 4; incorporated by reference in its entirety).

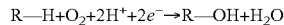

$$R-H + O_2 + 2H^+ + 2e^- \rightarrow R-OH + H_2O$$

Nature employs two types of MMOs: soluble MMO (sMMO), which utilizes a diiron cofactor; and particulate MMO (pMMO), which utilizes a dicopper cofactor (FIG. 1) (refs. 5, 6; incorporated by reference in their entireties). A major issue limiting the development of biological gas-to-liquid technology is the inability to express sMMO or pMMO in an industrially relevant host organism (refs. 1, 2; incorporated by reference in their entireties).

SUMMARY

Provided herein are soluble engineered polypeptides for oxidizing hydrocarbons, and methods of use, manufacture, and design thereof. In particular, soluble, polypeptides capable of oxidizing methane to methanol (e.g., hydroxylation) are provided.

In some embodiments, provided herein are compositions comprising a polypeptide capable of converting an alkane into an alkanol and/or an alkene to an epoxide. In some embodiments, the polypeptide is capable of converting methane into methanol. In some embodiments, the polypeptide is capable of converting propylene into propylene oxide. In some embodiments, the polypeptide carries out the hydroxylation of the alkane. In some embodiments, the polypeptide carries out the hydroxylation of the methane. In some embodiments, the polypeptide comprises a metal dependent oxygenase with an engineered active site. In some embodiments, the polypeptide is expressed in an industrially-relevant host organism and at a commercially-relevant scale. In some embodiments, the polypeptide comprises two domains, each with at least 60% sequence identity (e.g., >60%, >70%, >75%, >80%, >90%, >95%, >98%, >99%) with a domain of pmoB. In some embodiments, the polypeptide comprises S1-D1-linker-D2-S2, S1-D1-linker-D2, D1-linker-D2-S1, wherein S1 is a first soluble peptide, D1 is a polypeptide segment with at least 60% sequence identity (e.g., >60%, >70%, >75%, >80%, >90%, >95%, >98%, >99%) with a first soluble domain of pmoB, linker is a soluble peptide linker, D2 is a polypeptide segment with at least 60% sequence identity (e.g., >60%, >70%, >75%, >80%, >90%, >95%, >98%, >99%) with a second soluble domain of pmoB, and S2 is a second soluble peptide. In some embodiments, the polypeptide comprises at least 60% sequence identity (e.g., >60%, >70%, >75%, >80%, >90%, >95%, >98%, >99%) with spmoB7, sumo-spmoB7, and/or sumo-spmoB7 8pt3.

In some embodiments, provided herein are methods of converting an alkane (e.g., methane) into an alkanol (e.g., methanol) comprising exposing the alkane to a polypeptide described herein.

In some embodiments, provided herein are cells expressing a polypeptide described herein.

In some embodiments, provided herein are methods of biofuel production comprising exposing an alkane (e.g., methane) to a polypeptide described herein to produce an alkanol (e.g., methanol).

In some embodiments, provided herein are soluble polypeptides capable of converting an alkane into an alkanol comprising a core sequence comprising at least 60%, but less than 100% sequence identity (e.g., 60%, 65%, 70%, 75%, 80%, 85%, 90%, 95%, 99%, ranges there between) with SEQ ID NO: 23, the core sequence being C-terminally- and/or N-terminally-flanked by one or more soluble peptide segments. In some embodiments, the polypeptide is capable of converting methane into methanol. In some embodiments, the polypeptide carries out the hydroxylation of the alkane. In some embodiments, the polypeptide comprises a copper oxidase with an engineered active site. In some embodiments, the polypeptide is expressed in an industrially-relevant host organism and at a commercially-relevant scale. In some embodiments, the one or more soluble peptide segments are selected from peptides having at least 60% (e.g., 60%, 65%, 70%, 75%, 80%, 85%, 90%, 95%, 100%, ranges therein) sequence identity with one or SEQ ID NOS: 16, 17, 18, 21, and 22. In some embodiments, the soluble polypeptide comprises at least 60% sequence identity (e.g., 60%, 65%, 70%, 75%, 80%, 85%, 90%, 95%, 100%, ranges therein) with spmoB7 (SEQ ID NO: 13), sumo-spmoB7 (SEQ ID NO: 14), and/or sumo-spmoB7 8pt3 (SEQ ID NO: 13), but less than 100% sequence identify from a naturally-occurring sequence.

In some embodiments, provided herein are system comprising the soluble polypeptides capable of converting an alkane into an alkanol described herein. In some embodiments, systems comprise a fixed support selected from the list consisting of: a yeast cell, a phage, and a functionalized bead.

In some embodiments, provided herein are bioreactors comprising the soluble polypeptides capable of converting an alkane into an alkanol described herein.

DEFINITIONS

Figure 1:
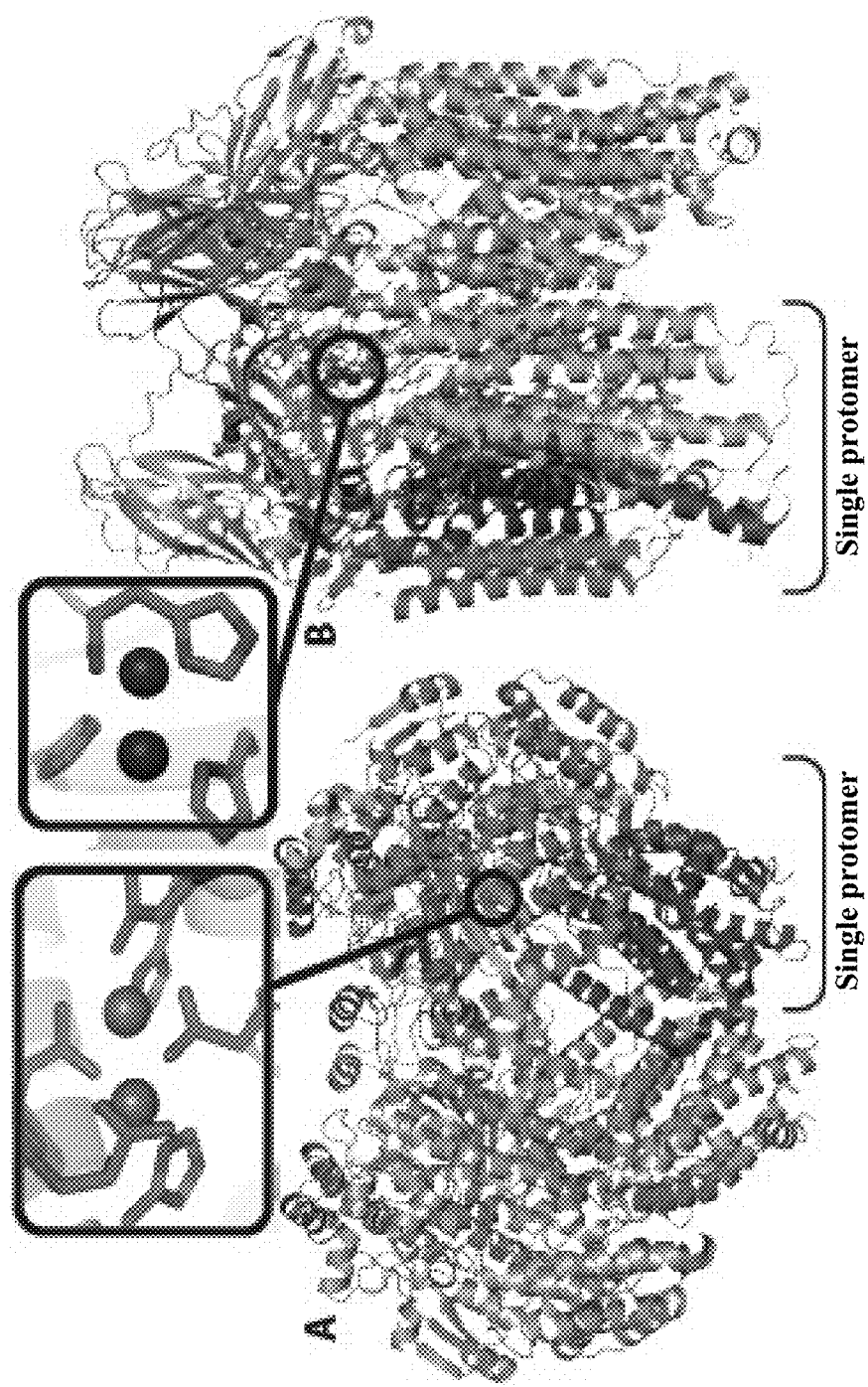
FIG. 1. (A) Crystal structure of sMMO (PDB code 4GAM). (B) Crystal structure of pMMO (PDB code 3RGB). Iron (A) and copper (B) ions are shown as spheres.

As used herein, the term "peptide" refers a short polymer of amino acids linked together by peptide bonds. In contrast to other amino acid polymers (e.g., proteins, polypeptides, etc.), peptides are of about 50 amino acids or less in length. A peptide may comprise natural amino acids, non-natural amino acids, amino acid analogs, and/or modified amino acids.

As used herein, the term "polypeptide" refers a polymer of amino acids, linked together by peptide bonds, that is over about 50 amino acids or less in length. A polypeptide may comprise natural amino acids, non-natural amino acids, amino acid analogs, and/or modified amino acids.

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Naturally occurring residues may be divided into classes based on common side chain properties, for example: polar positive (histidine (H), lysine (K), and arginine (R)); polar negative (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs.

Non-conservative substitutions (e.g., not conservative or semi-conservative) involve the exchange of an amino acid of one class or group for an amino acid from another class or group.

As used herein, the term "sequence identity" refers to the degree to which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative (e.g., "conservative sequence similarity") and/or semi-conservative (e.g., "semi-conservative sequence similarity") amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

As used herein, the term "physiological conditions" encompasses any conditions compatible with living cells, e.g., predominantly aqueous conditions of a temperature, pH, salinity, chemical makeup, etc. that are compatible with living cells.

The term "soluble", particularly when used in reference to peptide, polypeptide or protein, as used herein refers to the characteristic of being substantially, completely dissolvable in aqueous solution, under, for example physiological conditions. For example, soluble polypeptide typically lacks any transmembrane segments.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Sample may also refer to cell lysates or purified forms of the peptides and/or polypeptides described herein. Cell lysates may include cells that have been lysed with a lysing agent or lysates such as rabbit reticulocyte or wheat germ lysates. Sample may also include cell-free expression systems. Such examples are not however to be construed as limiting the sample types applicable to the present invention.

As used herein, the term "bioreactor" refers to any vessel in which a chemical process or reaction (e.g., conversion of an alkane (e.g., methane) into an alkanol (e.g., methanol), etc.) is carried out which involves organisms or biochemically active substances (e.g., enzymes or polypeptides capable or advancing a chemical reaction without turnover). Process within a bioreactor may be aerobic or anaerobic. A bioreactor can be of any size so long as it is useful for the culturing of cells and/or the performance of the desired chemical reaction. Typically, the bioreactor will be at least 1 liter and may be 10, 100, 250, 500, 1,000, 2,500, 5,000, 8,000, 10,000, 12,000 liters or more, or any volume in between. In some embodiments, the internal conditions of the bioreactor, including, but not limited to pressure, pH and temperature, are optionally controlled during the culture and/or reaction period. A bioreactor is composed of any material that is suitable for holding the bioreactive components (e.g., media, reactants, products, etc.) under appropriate conditions, such as glass, plastic or metal. A bioreactor may also comprise one or more ports, vents, valves, etc. for the additional and/or removal (e.g., selective additional and/or removal) or products, reactants, etc.

DETAILED DESCRIPTION

Provided herein are soluble engineered polypeptides for oxidizing hydrocarbons, and methods of use, manufacture, and design thereof. In particular, soluble, polypeptides capable of oxidizing methane to methanol (e.g., hydroxylation) are provided.

pMMO is a membrane bound α3β3γ3 homotrimer with protomers of three polypeptides: pmoA, pmoB, and pmoC (ref. 7; incorporated by reference in its entirety). The active site of pMMO is a dicopper site that resides in the N-terminal soluble domain of pmoB (ref. 5; incorporated by reference in its entirety) pmoB contains two soluble domains, an N-terminal cupredoxin domain and a C-terminal cupredoxin domain, connected in the middle by two transmembrane helices (ref 7; incorporated by reference in its entirety). It has been demonstrated that the two-transmembrane helices of pmoB can be replaced with an artificial linker and expressed in E. coli (ref. 5; incorporated by reference in its entirety). This protein, commonly referred to as spmoB, expresses as insoluble protein that can be refolded in the presence of copper to obtain active protein. The refolded protein is relatively unstable and obtained in extraordinarily low yields (ref 5; incorporated by reference in its entirety). In some embodiments, a protein within the scope herein does not require in vitro refolding and/or in vitro metal loading. In some embodiments, protein within the scope herein is active inside of an industrially relevant host organism (e.g., E. coli).

Using spmoB as a template, several computational protein design strategies were used to design in silico libraries to improve protein solubility. These strategies included: (1) designing the composition, length, and cutpoints for the linker between the two fragments of spmoB for improved stability and solubility, (2) stabilizing the hydrophobic core by identifying buried cavities and reducing their number and size, (3) redesigning the surface to reduce the number and size of hydrophobic patches, and (4) designing soluble fusion partners for N-terminus and C-terminus. Libraries encoding 2000 variants were screened for solubility and 5 variants with estimated expression yields of more than 10 mg/L in plasmid-based E. coli-based expression systems were obtained. Variants with expression levels as high as 30 mg/L were obtained. Purification of a variant referred to as spmoB7 was carried out and activity assays indicate this variant oxidizes methane to methanol. Additional variants, sumo-spmoB7 and sumo-spmoB7 8pt3, were also shown to be active using isotopically-labeled methane. Reconstitution of the copper cofactor is carried out using an in vivo copper loading method (see Examples). spmoB7 is isolated from the soluble fraction of an E. coli lysate (no refolding necessary) and no additional modifications of the protein are needed to obtain activity. In some embodiments, the protein is in an active, functional, and/or folded state in vivo. In some embodiments, this variant is routinely isolated at expression levels above 5 mg/L (e.g., >10 mg/L>20 mg/L, >30 mg/L, >50 mg/L, or more).

Experiments conducted during development of embodiments of the present invention demonstrate that computational and screening methods used herein produced protein sequences resulting in active soluble fragments of pMMO, and indicate that other variants with sequences described below also oxidize methane (See Examples).

Embodiments described herein find use in a variety of applications, not limited to the following:
  Methanol production from methane—proteins described herein are used, for example, in conjunction with other biochemical pathways to enable utilization of methane via a methanol-dependent pathway for biofuel production in either cell-free systems or in vivo systems.
  General oxidation chemistries—Since the chemistry performed by the protein described herein has not been previously demonstrated using recombinant proteins without in vitro refolding or metal loading, there are many alternative applications that stem from the construction of these polypeptides.

Provided herein are soluble engineered polypeptides for oxidizing hydrocarbons, and methods of use, manufacture, and design thereof. In particular, soluble, polypeptides capable of oxidizing methane to methanol (e.g., hydroxylation) are provided.

In some embodiments, soluble engineered polypeptides comprise a first polypeptide having at least 60% sequence identity with a first soluble domain of pmoB linked (via a linker peptide) to a second polypeptide having at least 60% sequence identity with a first soluble domain of pmoB. In some embodiments, the first and second polypeptides are artificial sequences (e.g., not naturally-occurring) having less than 100% sequence identity with a naturally occurring pmoB sequence.

In some embodiments, soluble engineered polypeptides further comprise one or more soluble peptide sequences (e.g., sumo, set12, mbp, etc.) linked (directly or via a linker peptide) to the pmoB-like polypeptide domains. In some embodiments, a soluble peptide is attached to the C-terminus and/or N-terminus of the soluble engineered polypeptides.

In some embodiments, soluble engineered polypeptides comprise, a first soluble peptide portion (S1) (SEQ ID NOs: 16, 17, 18, 21, and/or 22; or variants thereof), two linked pmoB-like polypeptide domains (D1-linker-D2) (SEQ ID NO: 23; or variants thereof), and a second soluble peptide portion (S2) (SEQ ID NOs: 16, 17, 18, 21, and/or 22; or variants thereof). Polypeptides may comprise additional soluble peptides and/or linkers. In some embodiments, a soluble engineered polypeptide comprises S1-D1-linker-D2-S2.

In some embodiments, soluble engineered polypeptides comprise a portion with at least 60% but less than 100% sequence identity (e.g., 60%, 65%, 70%, 75%, 80%, 85%, 90%, 95%, 96%, 97%, 98%, 99%) with SEQ ID NO: 23. In some embodiments, the polypeptides further comprise one or more soluble peptide sequences (e.g., sumo, set12, mbp, etc.) linked (directly or via a linker peptide) to the C-terminus and/or N-terminus of SEQ ID NO: 23. In some embodiments, the soluble peptide sequences comprise at least 60% (e.g., 60%, 65%, 70%, 75%, 80%, 85%, 90%, 95%, 100%) sequence identity with one of SEQ ID NOs: 16, 17, 18, 21, or 22.

In some embodiments, soluble engineered polypeptides comprise a portion with at least 60% but less than 100% (e.g., 60%, 65%, 70%, 75%, 80%, 85%, 90%, 95%, 96%, 97%, 98%, 99%) sequence similarity (e.g., semi-conservative or conservative) with SEQ ID NO: 23. In some embodiments, the polypeptides further comprise one or more soluble peptide sequences (e.g., sumo, set12, mbp, etc.) linked (directly or via a linker peptide) to the C-terminus and/or N-terminus of SEQ ID NO: 23. In some embodiments, the soluble peptide sequences comprise at least 60% (e.g., 60%, 65%, 70%, 75%, 80%, 85%, 90%, 95%, 96%, 97%, 98%, 99%) sequence similarity (e.g., semi-conservative or conservative) with one of SEQ ID NOs: 16, 17, 18, 21, or 22.

In some embodiments, all or a portion of the polypeptides and peptide segments within the scope herein comprise at least 60% (e.g., 60%, 65%, 70%, 75%, 80%, 85%, 90%, 95%, 96%, 97%, 98%, 99%) sequence identity and/or similarity with one or more of SEQ ID NOS:10-23. In some embodiments, a soluble engineered polypeptide or a portion thereof comprises at least one substitution (e.g., 1, 2, 3, 4, 5, 6, 7, 8, 9, 10, 11, 12, 13, 14, 15, 16, 17, 18, 19, 20, or more, or ranges there between) relative to one of SEQ ID NOS: 10-23.

EXAMPLES

Methane/Propylene Oxidation Assay Results

Figure 2:
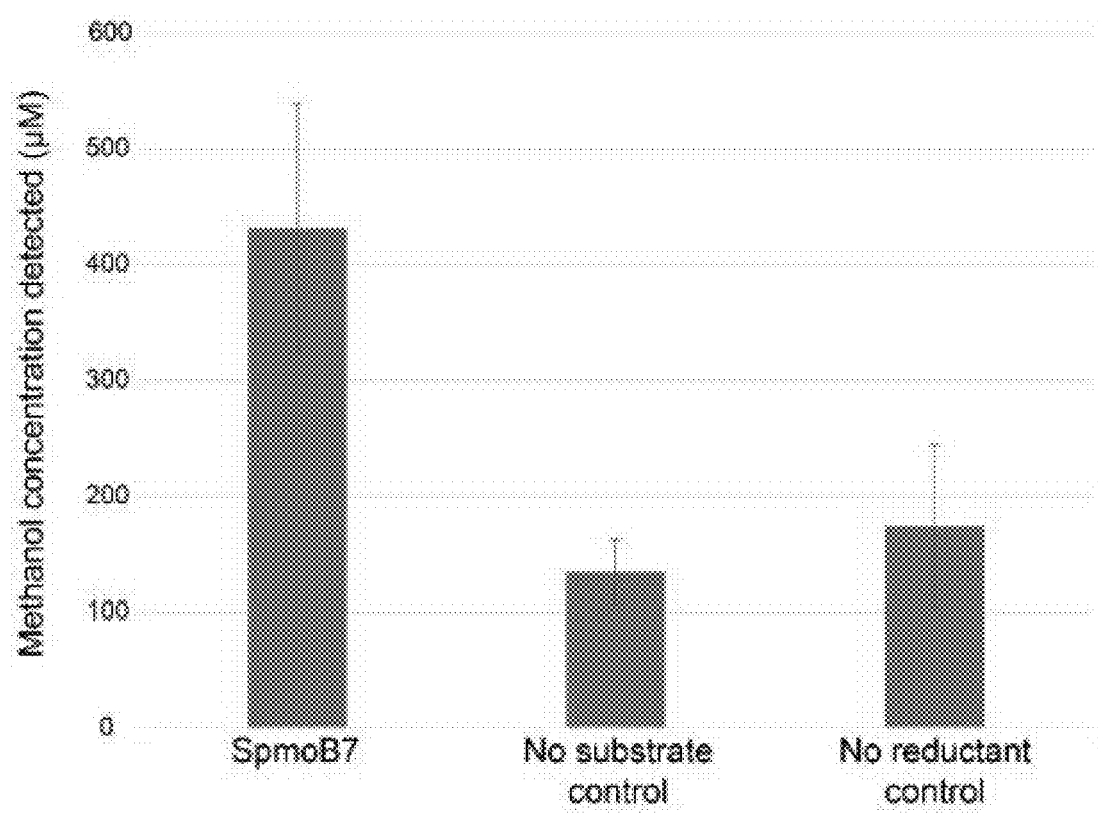
FIG. 2. SpmoB7 activity assays and controls.
Figure 3:
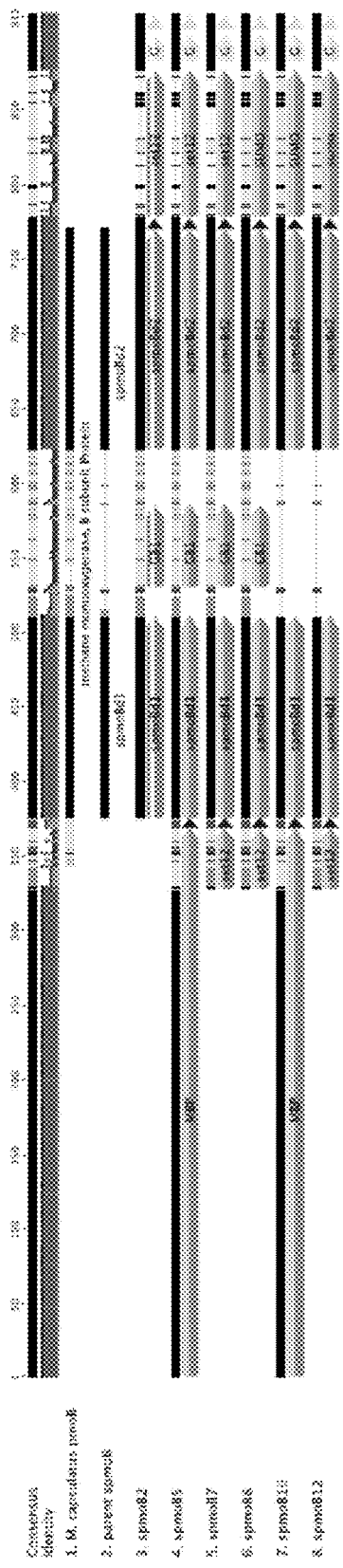
FIG. 3. Sequence alignments of variants.
Figure 4:
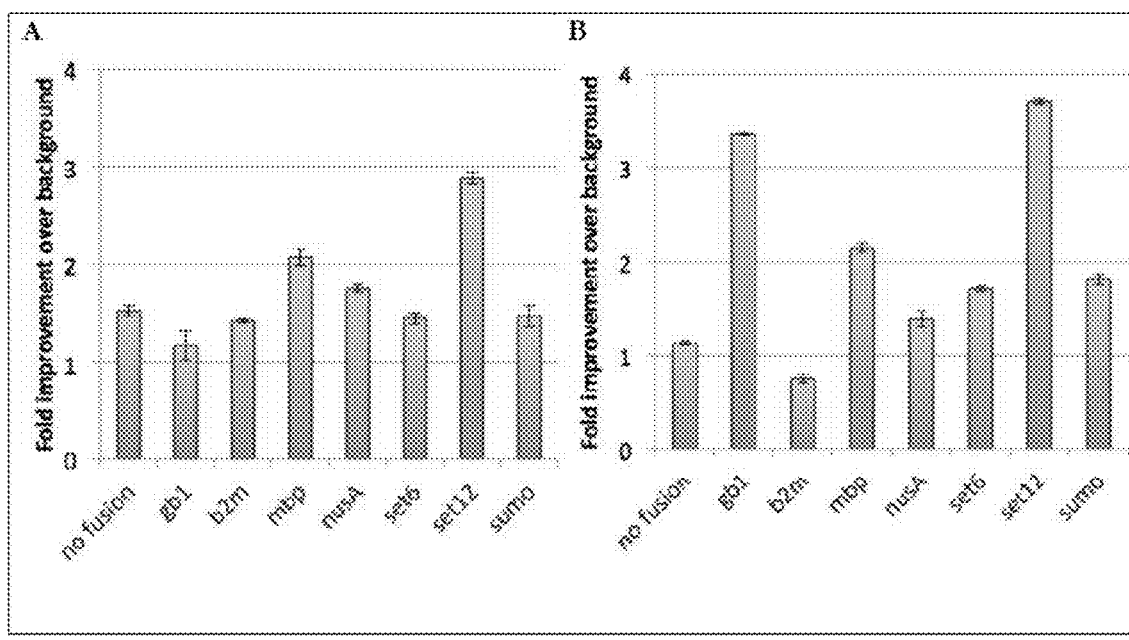
FIG. 4. Improvements in soluble expression of N- and C-terminal fusions of spmoB. (A) N-terminal fusions. (B) C-terminal fusions.
Figure 9:
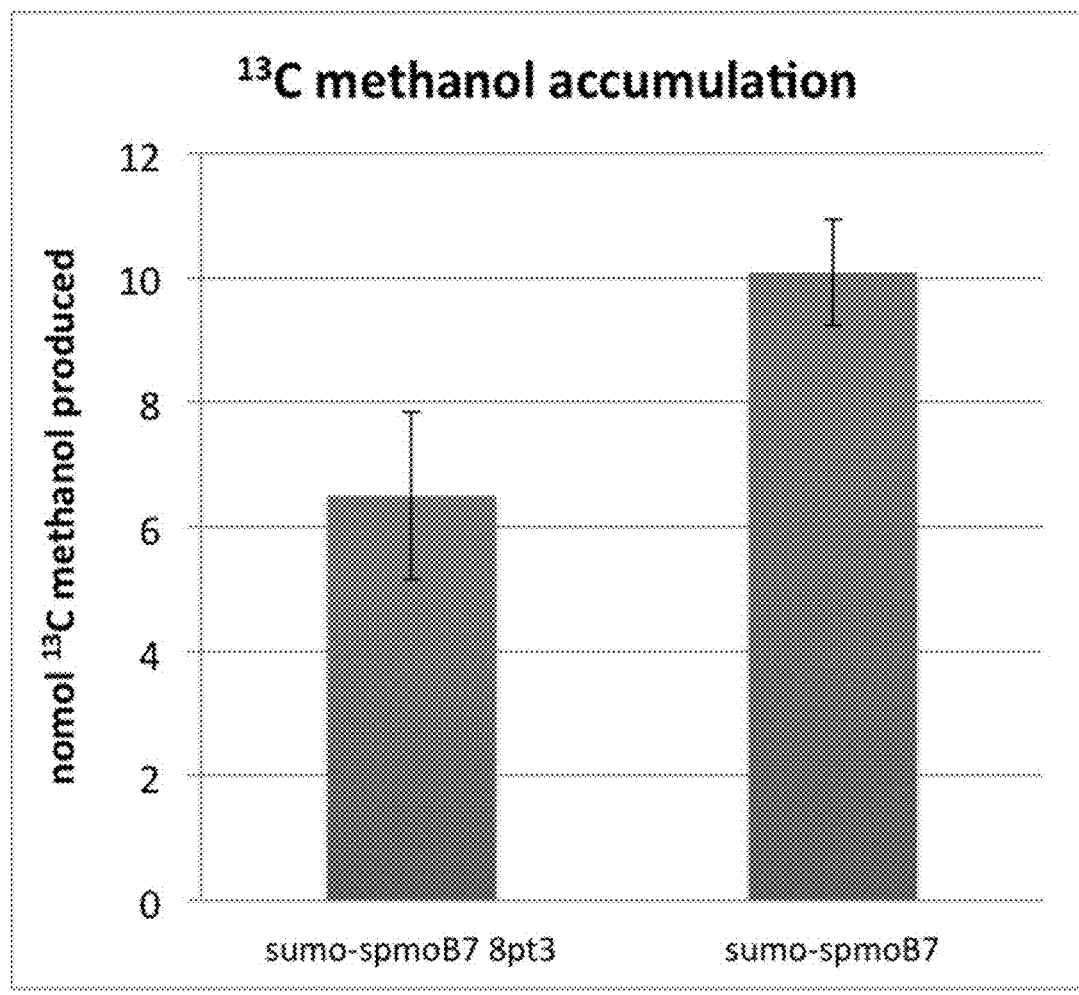
FIG. 9. $^{13}C$ methanol production by selected variants

Experiments were conducted during development of embodiments of the present invention to demonstrate monooxygenase activity by detecting the oxidation of propylene to propylene oxide (PO). In MMO activity assays, PO is frequently detected instead of methanol because of PO's low background in typical biological solutions and its relative ease of detection (ref 5; incorporated by reference in its entirety). Table 1 shows that several variants were capable of oxidizing propylene. SpmoB7 was subsequently assayed for methane oxidation and was found to be capable of producing methanol as well (FIGS. 2 and 9, Table 2, and SEQUENCES). The methane oxidation measurements have considerable measurement error due to the difficulty of measuring methanol production at low levels. To overcome this obstacle and to conclusively show methanol is being produced from methane, activity of an spmoB7 variant with an N-terminally encoded sumo tag and a similar construct with additional point mutations were measured using isotopically labeled methane (FIG. 9). The spmoB7, sumo-pmoB7, and sumo-spmoB7 8pt3 variants are the first examples of engineered fragments of pmoB that express solubly in *E. coli* and are active without refolding.

TABLE 1

Summary of purified spmoB data collected during the granting period.

| Variant | Cu ions per protein | Soluble expression yield (mg/L) | Propylene oxidation activity (min$^{-1}$) | Methane oxidation activity (min$^{-1}$) |
|---|---|---|---|---|
| parent spmoB | 5.4 (n = 2) | Negligible | 0.086 ± 0.037 | 0.20 ± 0.020* |
| spmoB2 | — | 11.4 | 0.035 ± 0.0035 | — |
| spmoB5 | 2.5 ± 0.3 (n = 2) | 32.1 | 0.022 ± 0.0074 | — |
| spmoB7 | 0.7 ± 0.04 (n = 3) | 17.3 | 0.028 ± 0.014 | 0.057 ± 0.051 |
| spmoB8 | — | Negligible | — | — |
| spmoB10 | — | 6.0 | — | — |
| spmoB12 | — | 15.1 | 0.031 ± 0.029 | — |
| sumo spmoB7 | — | 6.5 | — | See FIG. 9 |
| sumo spmoB7 8pt3 | — | 5.4 | — | See FIG. 9 |

*Literature values reported under different conditions.

TABLE 2

Glossary of spmoB variant labels. The second column ("Nomenclature") defines the variant architecture using a common nomenclature that is read from N-terminus to C-terminus, "D11" and "D2" correspond to domains 1 and 2, respectively, "Mc-6" and "pmoA-gb1" are linker constructs that are defined in Table 3. "mbp," "set12," and "sumo" are domain fusions; if a domain fusion label appears on the left of "D1," then it is an N-terminal fusion, and if on the right of "D2," a C-terminal fusion.

| Label | Nomenclature | Description/Notes |
|---|---|---|
| spmoB | D1-D2 | pmoB subunit of *M. capsulatus* (Bath) pMMO |
| Mc-6 | D1-Mo-6-D2 | spmoB with GEPSGEPS linker (SEQ ID NO: 1) |
| pmoA-gb1 | D1-pmoA-gb1-D2 | spmoB with GEPS-gb1-GE-pmoA-GS linker (SEQ ID NO: 2) |
| set12 | D1-Mc-6-D2-set12 | Mc-6 with C-terminal fusion |
| spmoB2 | D1-pmoA-gb1-D2-set12 | pmoA-gb1- with C-terminal fusion; measured PO and MMO activity |
| spmoB5 | mbp-D1-pmoA-gb1-D2-set12 | pmoA-gb1 with double fusion; measured PO and MMO activity |
| spmoB7 | set12-D1-pmoA-gb1-D2-set12 | pmoA-gb1 with double fusion; mearured PO and MMO activity |
| spmoB8 | set12-D1-pmoA-gb1-D2-sumo | pmoA-gb1 with double fusion; measured PO and MMO activity |
| spmoB10 | mbp-D1-Mo-6-D2-sumo | Mc-6 with double fusion; measured PO and MMO activity |
| spmoB12 | set12-D1-Mc-6-D2-sumo | Mc-6 with double fusion; measured PO and MMO activity |
| FC | D1-Mc6-D2-set12 + M298F/M300C | set12 with M298F/M300C |
| sumo spmoB7 | set12-sumo-D1-pmoA-gb1-D2-set12 | spmoB7 with additional N-terminal fusion |

Generation of Models of Parent spmoB

The original parent spmoB construct (ref. 5; incorporated by reference in its entirety), is derived from the pmoB subunit of *Methylococcus capsulatus* Bath (Mc) pMMO. The spmoB construct contains residues 22-172 and 256-414 of pmoB connected by a flexible Gly-Lys-Leu-Gly-Gly-Gly (GKLGGG) linker (SEQ ID NO: 3). Because no crystal structure of spmoB exists, a structural model for spmoB was generated using the loop modeling feature of TRIAD, Protabit's proprietary computational protein design software suite. The model was constructed by removing the two transmembrane helices (residues 172-265) from the coordinate file of pmoB derived from the crystal structure of holo-pMMO (PDB ID: 3RGB) (ref. 8; incorporated by reference in its entirety) and modeling the flexible linker into the resulting gap; TRIAD was used to find the lowest energy conformation and placement of the linker relative to the rest of spmoB.

Linker Designs for Improved Stability/Solubility

The initial linker inserted between the two domains of the parent spmoB is a six residue GKLGGG linker (SEQ ID NO: 3), which was designed by visual inspection of the holo-pMMO structure (ref. 5; incorporated by reference in its entirety). Detailed modeling of the spmoB linker region identified several opportunities for improvement. First, molecular dynamics (MD) analysis of the parent spmoB predicts that the linker is the most flexible part of the construct; a highly flexible linker may contribute to the low soluble expression of spmoB. To reduce flexibility, linkers with more complex sequences are used. Several higher-complexity sequences including Gly, Ser, Glu, and Pro amino acid types and also small proteins or protein fragments were tested (Table 3). Second, if the regions on either side of the linker are considered in addition to the linker itself, a flexible 14-residue tether connects the two structured regions of spmoB. In some embodiments, the flexibility of this region is reduced overall by decreasing the size of the tether. Thus, in addition to the cutpoints for the original linker at residues 172 and 265, a second set of cutpoints was selected at residues 169 and 267, reducing the length of the tether by 5 residues.

cutpoints. Linkers of length 6 and higher did not show signs of strain and some were even predicted to form short secondary structure elements.

Seven short Gly/Ser and Gly/Ser/Glu/Pro linkers were constructed and evaluated for their effect on the soluble expression of spmoB (Table 2, Mc-1 to Mc-7). Soluble expression screening with the split-GFP assay (described below (ref 10; incorporated by reference in its entirety)) indicated that construct Mc-6 had the highest soluble expression of the group, with a marginal improvement in soluble expression over the parent. Further rounds of engineering were executed using Mc-6 as the background template.

A simple structure-based approach was used to recapitulate a more native-like linker between the two domains of spmoB. Using the crystallographic information from 3RGB and 3RFR (pMMO from *Methylocystis* sp. strain M) as a guide, a sequence from a soluble region of pmoA that interacts with pmoB was selected and incorporated as a natural linker between the two domains in the pmoB subunit. To achieve this, the cutpoint of pmoB was moved from residue 169 to 182, the construct was appended with a Gly-Glu-Pro-Ser linker, and an additional Gly-Ser linker was attached N-terminally to the cutpoint at residue 267.

The new linker and cutpoints create an empty 15 Å space from residue 182 of pmoB to where the pmoA subunit interacts with pmoB for 33 residues. Three different molecular entities were sampled at the 15 Å space: the soluble GB1 domain (ref 10; incorporated by reference in its entirety), beta-2-microglobulin (b2m) (ref 11; incorporated by reference in its entirety), and an extended b2m linker (ref 11; incorporated by reference in its entirety). The GB1 domain

TABLE 3

Linkers designed and tested.

| Name | Cutpoints | Linker | Length | Type |
| --- | --- | --- | --- | --- |
| Parent spmoB | 173-265 | GKLGGG (SEQ ID NO: 3) | 6 | Original linker |
| Mc-1 | 172-263 | GSGSG (SEQ ID NO: 4) | 5 | Gly/Ser |
| Mc-2 | 172-263 | GSGSGS (SEQ ID NO: 5) | 6 | Gly/Ser |
| Mc-3 | 172-263 | GSGSGSG (SEQ ID NO: 6) | 7 | Gly/Ser |
| Mc-4 | 169-267 | GSGSGSG (SEQ ID NO: 6) | 7 | Gly/Ser |
| Mc-5 | 169-267 | GSGSGSGS (SEQ ID NO: 7) | 8 | Gly/Ser |
| Mc-6 | 169-267 | GEPSGEPS (SEQ ID NO: 1) | 8 | Gly/Ser/Glu/Pro |
| Mc-7 | 169-267 | GSGEPSGS (SEQ ID NO: 8) | 8 | Gly/Ser/Glu/Pro |
| pmoA-gb1 | 182-267 | GEPS-gb1-GE-pmoA-GS (SEQ ID NO: 2) | 96 | pmoA + domain |
| pmoA-b2m | 182-267 | GEPS-b2m-GE-pmoA-GS (SEQ ID NO: 2) | 139 | pmoA + domain |
| pmoA-b2mL | 182-267 | GEPS-b2mL-GE-pmoA-GS (SEQ ID NO: 2) | 189 | pmoA + domain |

* the sequence of the pmoAlinker is PVEYNGMLMSIADIQGYNYVRTGTPEYIRMVEK(SEQ ID NO: 9)

Several Gly/Ser and Gly/Ser/Glu/Pro linkers ranging in length from 4 to 11 residues were evaluated with TRIAD's loop modeling feature, which uses inverse kinematics (ref. 9; incorporated by reference in its entirety) and multiple rounds of relaxation to predict the most likely conformation and position of each linker relative to the rest of spmoB. Linkers containing less than 5 residues were found to be strained or not able to span the distance between the fixed proved to be the most soluble of the three by the split-GFP assay on the spmoB Mc-6 template. This construct was named spmoB pmoA-gb1, and was later incorporated into downstream versions of the protein.

N- and C-Terminal Fusion Designs

Figure 5:
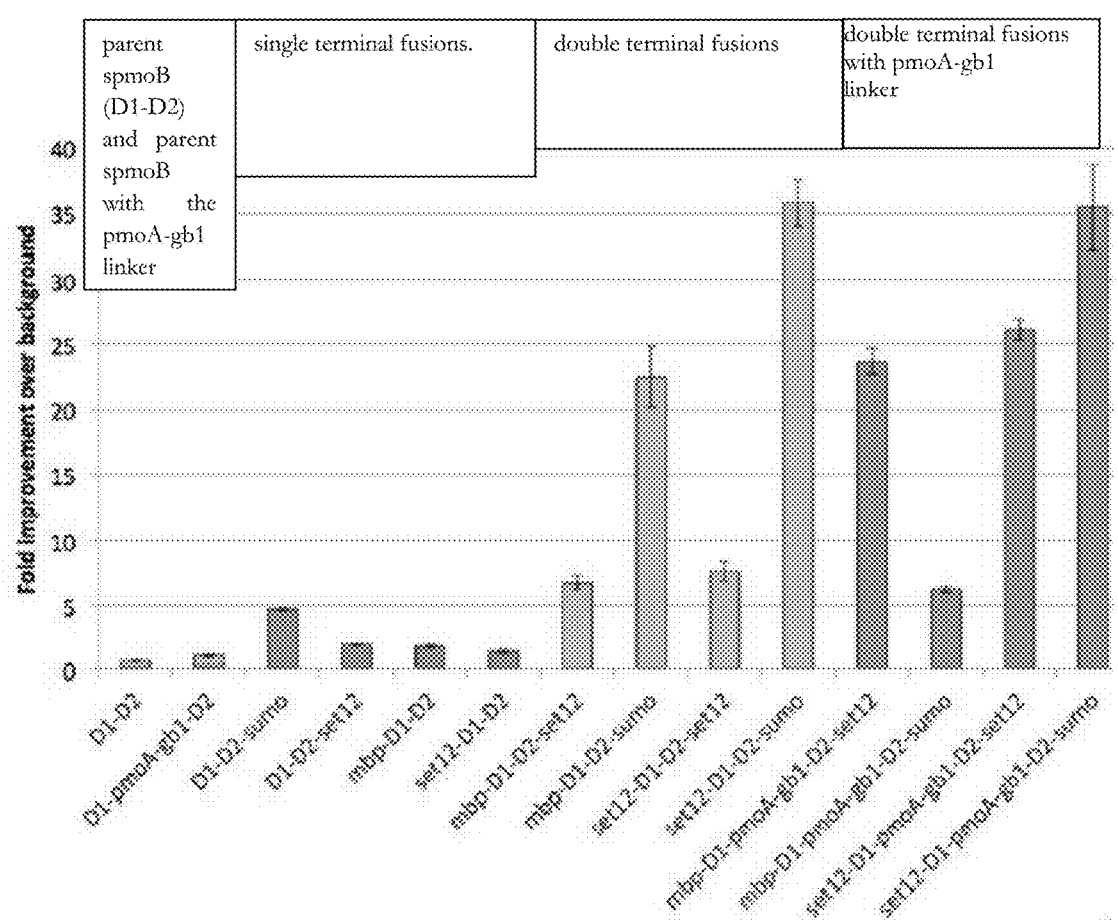
FIG. 5. Improvement in soluble expression of multi-domain fusions of spmoB.

A wide range of soluble protein domains were investigated for their effects on spmoB expression at both the N- and the C-termini. These domains included GB1 (ref 10;

incorporated by reference in its entirety), b2m (ref. 11; incorporated by reference in its entirety), maltose binding protein (mbp), N-utilising substance A (NusA) (ref. 12; incorporated by reference in its entirety), small ubiquitin-like modifier (sumo) protein (ref. 12; incorporated by reference in its entirety), and two versions of highly charged peptides originating from the bacteriophage T7 minor capsid protein 10B (set6 and set12) (ref 12; incorporated by reference in its entirety). These domains were selected for their known performance as solubility-enhancing factors either from the literature (refs. 10-12; incorporated by reference in their entireties) or from in-house experiments. A split-GFP soluble expression assay showed that fusions containing GB1, sumo, mbp, and set12 yielded the best results overall (FIG. 5), and fusions to the C-terminus were, in general, more effective than fusions to the N-terminus.

Figure 6:
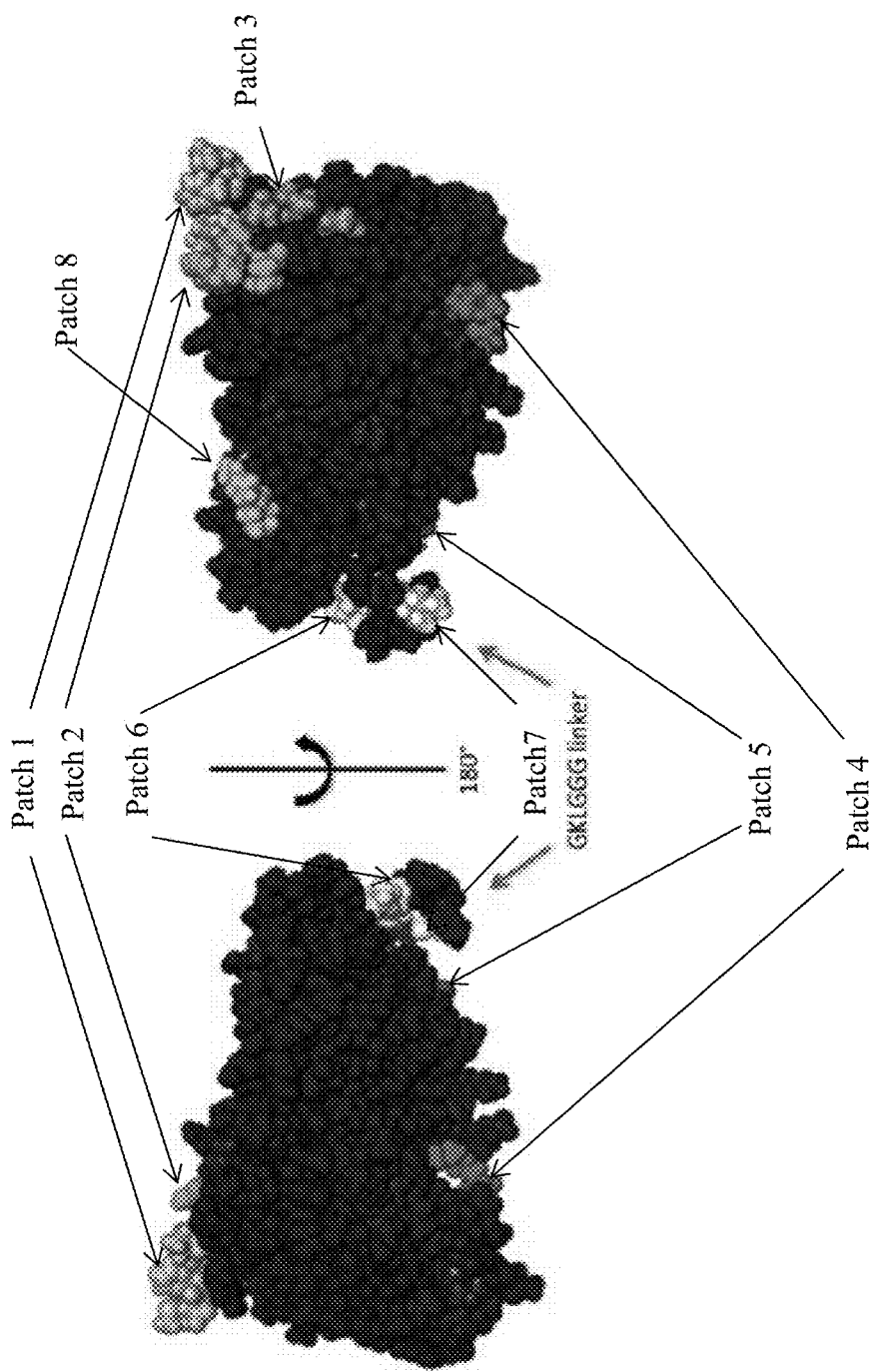
FIG. 6. Hydrophobic patches identified on spmoB by TRIAD using the SAP algorithm. Patch 1: V293, P294, F413, M414; Patch 2: I380, Y381, P383; Patch 3: P408, P411, I410; Patch 4: P280, L277, A279, P278; Patch 5: L109, P111; Patch 6: P169, V170; Patch 7: L175; Patch 8: P94, P96, G95.

This first round of data informed a second round of domain fusion experiments, in which two fusion protein domains were attached to the parent spmoB protein, one at each terminus (FIG. 6). Four double-fusion constructs were made, featuring either mbp or set12 at the N-terminus and set12 or sumo at the C-terminus. An additional four constructs were made with identical N- and C-terminal fusions, but with the Mc-6 linker replaced with the pmoA-gb1 linker described above. These combination constructs showed the further improved soluble expression of the spmoB variants (FIG. 6), and six of these variants were selected for large-scale expression and further characterization.

Designs to Improve the Stability of spmoB

A strategy for improving the stability of spmoB was to optimize packing within the protein's core. Poorly packed residues were identified using three analysis methods in TRIAD. First, statistical residue energy (SRE) analysis, a proprietary multicomponent scoring function, was used to identify residues that are not compatible with their environment in the protein. This method also identifies sub-optimal residues on the protein's surface. Second, the interstitial space between the atoms in the solvent-excluded interior of the protein (solvent excluded volume) for each residue was compared to a statistical distribution of volumes from a database of thermophilic and mesophilic protein structures (ref. 13; incorporated by reference in its entirety). Third, positions where point mutations are predicted by molecular mechanics force fields to improve the stability of the protein were identified with a ΔΔG scan using FoldX (ref. 14; incorporated by reference in its entirety) and TRIAD ΔΔG with the Rosetta (ref. 16; incorporated by reference in its entirety) and Phoenix (ref. 17; incorporated by reference in its entirety) forcefields.

The residues identified by the three methods were probed by single or double site-saturation mutagenesis as shown in Table 4. Subsequently, combinatorial sequence designs were carried out to optimize regions surrounding poorly packed "seed" residues within the core of spmoB, which were identified based on a consensus of packing quality based on SRE and solvent excluded volume (Table 5).

TABLE 4

Summary of spmoB single and double site stability libraries tested. Positions were identified by core packing, SRE, or ΔΔG analysis.

| Positions | Degenerate codon | Amino acid types represented | Design strategy |
| --- | --- | --- | --- |
| K36 | NNS | all | SRE |
| E66 | NNS | all | ΔΔG |
| G76 | NNS | all | SRE |
| T80 | NNS | all | SRE/ΔΔG |
| L89 | DKS | R, C, G, I, L, M, F, S, W, V | Core |

TABLE 4-continued

Summary of spmoB single and double site stability libraries tested. Positions were identified by core packing, SRE, or ΔΔG analysis.

| Positions | Degenerate codon | Amino acid types represented | Design strategy |
| --- | --- | --- | --- |
| P96 | NNS | all | SRE |
| G107 | NNS | all | SRE |
| L109 | NNS | all | SRE |
| D123 | NNS | all | ΔΔG |
| D135 | NNS | all | SRE |
| H137 | NNS | all | ΔΔG |
| T140 | NNS | all | Core/ΔΔG |
| N143 | NNS | all | ΔΔG |
| Q145 | NNS | all | SRE |
| G146 | NNS | all | SRE/ΔΔG |
| G148 | NNS | all | SRE |
| M163 | NNS | all | SRE |
| T281 | NNS | all | ΔΔG |
| D288 | NNS | All | SRE/ΔΔG |
| M298 | DKS | R, C, G, I, L, M, F, S, W, V | Core |
| M300 | DKS | R, C, G, I, L, M, F, S, W, V | Core |
| N306 | NNS | all | ΔΔG |
| S321 | NNS | all | ΔΔG |
| I380 | NNS | all | SRE |
| S385 | NNS | all | ΔΔG |
| R400 | NNS | All | SRE |
| D406 | NNS | all | SRE/ΔΔG |
| L89/T140 | DKS/DBS | R, C, G, I, L, M, F, S, W, V/A, R, C, G, I, L, M, F, S, T, W, V | Core |
| M298/M300 | DKS/DKS | R, C, G, I, L, M, F, S, W, V/R, C, G, I, L, M, F, S, W, V | Core |

TABLE 5

Seed positions and nearby residues included in combinatorial sequence design calculations.

| Seed residues | Nearby residues included in design calculations |
| --- | --- |
| L52 | W49, W54, F124, Y336 |
| W54 | L52, I67, Y336 |
| I67 | W54, V65, V126, L128, T140 |
| L89 | W49, F124, V126, T140, M142 |
| T140 | I67, L89, F124 |
| M298 | A289, M300, A366, W371, L409 |
| W371 | M298, F324, L376 |

For each seed position, the surrounding positions within 3 Å that interact with the sidechain of the seed position were chosen for design (Table 4). The design positions were allowed to retain their wild-type identities or mutate to any nonpolar amino acid identity. For all sequence design calculations, special care was taken to avoid designing positions that are known to coordinate the monocopper site (H48, H72) or the dicopper active site (H33, H137, and H139).

Using TRIAD, combinatorial sequence designs were carried out with variable design parameters, and the resulting sequences were converted into degenerate codon libraries with a target size of 250 variants. These variant sequences were also evaluated and ranked by solvent excluded volume to identify variants with improved packing quality. Sequence designs with seeds L89, M298, and W371 were chosen for further analysis because these designs yielded variants with the best solvent excluded volume. The resulting degenerate codon libraries are shown in Tables 6, 7, and 8. In the first round of engineering, testing focused on the single and double mutants in Table 4, which yielded several hits (see Table 9). The combinatorial sequence design libraries in Tables 6, 7, and 8 are evaluated in subsequent rounds of laboratory screening.

TABLE 6

Degenerate codon library 1.

| Position | Library AAs | Degenerate codon |
|---|---|---|
| M298 | A, I, L, M, P, T, V | VYS |
| F324 | R, Y | TWC |
| L376 | A, C, D, E, F, G, H, I, K, L, M, N, P, Q, R, S, T, V, W | NBS + VNS |

TABLE 7

Degenerate codon library 2.

| Position | Library AAs | Degenerate codon |
|---|---|---|
| W49 | F, W | TTC + TGG |
| L89 | I, M | ATS |
| V126 | F, I, L, M, V | NTS |
| T140 | I, M, V| | RTS |
| M142 | I, L, M, V | VTS |

TABLE 8

Degenerate codon library 3.

| Position | Library AAs | Degenerate codon |
|---|---|---|
| M298 | F, I, M, V | NTS |
| M300 | F, I, L, M, V | NTS |
| W371 | C, F, L, R, W | YKS |
| L409 | L, M | MTG |

| Library | Library size | # screened | # sequenced | # hits | Hit amino acid identity |
|---|---|---|---|---|---|
| K36 | 20 | 96 | 12 | 5 | Q, V, P, E, M |
| E66 | 20 | 96 | 18 | 0 | — |
| G76 | 20 | 96 | 34 | 2 | R, E |
| T80 | 20 | 96 | 9 | 1 | E |
| P96 | 20 | 96 | 8 | 2 | G, A |
| G107 | 20 | 96 | 5 | 1 | W |
| L109 | 20 | 96 | 4 | 1 | D |
| D123 | 20 | 96 | 6 | 0 | — |
| H137 | 20 | 96 | 5 | 2 | E, D |
| T140 | 20 | 96 | 5 | 0 | — |
| N143 | 20 | 96 | 23 | 2 | G, S |
| G146 | 20 | 96 | 7 | 1 | D |
| G148 | 20 | 96 | 13 | 1 | L |
| M163 | 20 | 96 | 12 | 4 | G, C, R, L |
| T281 | 20 | 96 | 4 | 0 | — |
| D288 | 20 | 96 | 16 | 3 | S, E, N |
| V293 | 18 | 96 | 21 | 1 | A |
| S321 | 20 | 96 | 8 | 2 | G, H |
| I380 | 20 | 96 | 4 | 0 | — |
| S385 | 20 | 96 | 17 | 1 | G |
| R400 | 20 | 96 | 6 | 0 | — |
| D406 | 20 | 96 | 9 | 0 | — |
| I410 | 18 | 96 | 8 | 0 | — |
| L277/A279 | 324 | 768 | 28 | 1 | L/P |
| M298/ M300 | 144 | 384 | 5 | 3 | F/C, F/L, F/V |
| I380/Y381 | 324 | 768 | 38 | 6 | A/E, E/S, G/S, T/D, T/G, G/D |
| F413/ M414 | 324 | 768 | 41 | 7 | P/S, A/M, R/A, H/H, R/N, P/P, A/D |

Designs to Remove Hydrophobic Patches on the Surface of spmoB

To improve the solubility of spmoB, hydrophobic patches on the surface of spmoB were identified using the structure-based spatial aggregation propensity (SAP) algorithm (ref 17; incorporated by reference in its entirety). SAP calculations yielded eight hydrophobic patches as shown in FIG. 6. Many of the patches included prolines, which often serve important structural roles in proteins. Thus, proline positions were not mutated in any of the libraries. Three of the patches were excluded from consideration because of their location near or on the flexible linker that is being replaced in other variants (Patches 6 and 7), or because the patch is made up only of prolines and glycines, which often serve important structural roles and may be poor choices for design (Patch 8).

For each of the remaining patches, the degenerate codon VVW was chosen to replace the wild type residue at each position in the patch as shown in Table 10. This degenerate codon encodes 12 amino acids, which include all of the polar or charged amino acid types and was expected to improve the hydrophilicity at these positions on the surface of spmoB. Each position was mutated individually, resulting in 9 single site libraries; three combinations were also constructed for patches that have residues close in primary sequence (Table 10). L109 and 1380 were replaced with NNS instead of VVW because they were also identified by SRE as described above. Finally, residues F413 and M414 are located at the C-terminus of spmoB, which is exposed to the solvent. In addition to mutating these residues with the degenerate codon VVW, spmoB was truncated to remove either M414 or F413/M414.

TABLE 10

| Summary of spmoB single and double site solubility mutation libraries tested. | | | |
|---|---|---|---|
| Position | Patch # | Degenerate codon | Amino acid types represented |
| L109* | 5 | NNS | all |
| L277 | 4 | VVW | A, R, N, D, Q, E, G, H, K, P, S, T |
| A279 | 4 | VVW | A, R, N, D, Q, E, G, H, K, P, S, T |
| V293 | 1 | VVW | A, R, N, D, Q, E, G, H, K, P, S, T |
| I380* | 2 | NNS | all |
| Y381 | 2 | VVW | A, R, N, D, Q, E, G, H, K, P, S, T |
| I410 | 3 | VVW | A, R, N, D, Q, E, G, H, K, P, S, T |
| F413 | 1 | VVW | A, R, N, D, Q, E, G, H, K, P, S, T |
| M414 | 1 | VVW | A, R, N, D, Q, E, G, H, K, P, S, T |
| L277/A279 | 4 | VVW/VVW | A, R, N, D, Q, E, G, H, K, P, S, T/ A, R, N, D, Q, E, G, H, K, P, S, T |
| I380/Y381 | 2 | VVW/VVW | A, R, N, D, Q, E, G, H, K, P, S, T |
| F413/M414 | 1 | VVW/VVW | A, R, N, D, Q, E, G, H, K, P, S, T/ A, R, N, D, Q, E, G, H, K, P, S, T |

*indicates that position was also identified by SRE (Table 3)

Construction and Cloning of Initial spmoB Gene

The parent spmoB gene was cloned into pY71A(lc) using Gibson assembly (ref. 18; incorporated by reference in its entirety). The spmoB gene was cloned in frame with a C-terminal tag composed of a TEV cleavage site, (Gly3 Ser)2 linker, β-strand 11 of GFP (ref 19; incorporated by reference in its entirety), a Gly3 Ser linker and a Strep-tag (ref 20; incorporated by reference in its entirety). This arrangement of purification and split-GFP tags on the C-terminus was selected from a collection of tag arrangements that still exhibited the desired functionality of each tag. The combined tag was abbreviated to "TGS" and referenced as such within this document.

Construction of spmoB Variant Libraries

Variant libraries of spmoB were constructed using either the Q5® SDM Kit (NEB Inc., Ipswich, Mass., USA) or through megaprimer mutagenesis (ref. 21; incorporated by reference in its entirety). After transformation into BL21

Gold DE3 cells, colonies were picked on a Genetix Qbot into 384-well glycerol stock plates. Libraries were over-sampled by at least 3-fold, and in most cases almost 5-fold.

Soluble Expression Screen Development

To identify spmoB variants with improved solubility, an in vitro split-GFP system was employed (ref. 19; incorporated by reference in its entirety). 96-well 2 mL deep well plates containing 1 mL of autoinduction media were inoculated with individual library colonies. Cultures were grown for 16 hours at 28° C. with shaking at 350 RPM. Plates were then centrifuged and the pellets were stored at −20° C. Cells were lysed using a detergent-based lysis buffer. Clarified lysate containing the expressed spmoB variants (with a C-terminal β-strand 11 from GFP) was mixed with the GFP1-10 reagent, allowing the full-length GFP protein to become reconstituted and fluoresce. The detected GFP fluorescence is proportional to the amount of soluble protein; therefore, a brighter signal indicates more soluble spmoB is present in the lysate. The advantages of this assay include: (1) the minimal effect of the C-terminal GFP11 tag on solubility of the protein of interest, ensuring the response is due only to the protein of interest, and (2) the selectivity of the split-GFP interaction, allowing the assay to be performed in clarified cell lysate.

The split-GFP complementation assay was automated with a Tecan Evo liquid-handling robot, allowing for 768 unique clones to be examined in triplicate each day. Assay plates had a set of control wells containing clones with the empty pY71A(lc) plasmid, the parent spmoB-C-set12 gene, or an unrelated solubly-expressed protein as the negative, baseline, and positive controls, respectively. Over the course of the project, the GFP1-10 reagent requirement was reduced 4-fold through the use of high density microplates (384-well vs. 96-well). The cost of the lysis buffer was also reduced by 66% while maintaining effectiveness by decreasing the amount of a commercial lytic additive and supplementing it with an off-the-shelf detergent.

Soluble Expression Screen Results

After split-GFP analysis, potential hits were re-arrayed, re-cultured, and sent to Beckman Genomics for single pass sequencing. True hits were identified by matching results from the sequencing analysis and data from a secondary split-GFP assay. Results are shown in Table 9. Library construction and solubility screening Large Scale Growth, Purification, and Activity Assay of spmoB7

Eight constructs identified from domain fusion studies were selected for growth scale-up and purification (Table 1). Plasmids were transformed into *E. coli* strain C41(DE3) or BL21(DE3) and grown overnight on LB-agar plates containing ampicillin. Individual colonies were used to inoculate 1 L cultures of autoinduction media, then grown at 37° C. with shaking at 225 RPM. The growth temperature was changed to 20° C. at an OD600 of approximately 0.5. After 10 hours of growth, cells were transferred to 1 L centrifuge bottles along with 5 mL of sterile sugar solution and 5 mL of 1 M CuSO4. The sugar solution contains 125 g glycerol, 12.5 g glucose, and 50 g α-lactose monohydrate brought to a final volume of 500 mL with water. Resuspended cells were incubated for two hours at room temperature in sealed bottles. Cells were harvested by centrifugation and the cell pellet was flash frozen and stored at −80° C.

Frozen cell pellets were re-suspended in wash buffer (150 mM NaCl and 50 mM Tris base, pH 8.0) and lysed by sonication or chemical additives. Cellular debris was removed by ultracentrifugation at 40,000 RPM for 30 minutes. The resulting supernatant was applied to a streptactin column equilibrated with wash buffer using an FPLC. After extensive washing, the purified protein was eluted from the column using buffer containing 150 mM NaCl, 50 mM Tris base, 2.5 mM desthiolbiotin, and 10 mM MgCl2 at pH 8.0. Eluted protein was then analyzed using SDS-PAGE. The extinction coefficient, calculated by the program Geneious (Biomatters, Auckland, New Zealand) at 280 nm was used for all protein quantitation. Results indicate that four of the six constructs express at levels of >10 mg/L, with one (spmoB5) expressing at >30 mg/L (Table 1).

Metal Content Analysis of Hits

The activity of spmoB is contemplated to be dependent on both the correct coordination of copper ions within the active sites of the protein and the concentration of copper in the in vitro assay during methane oxidation; although the present invention is not limited to any particular mechanism of action and an understanding of the mechanism of action is not necessary to practice the present invention. The metal content of spmoB5 and spmoB7 were therefore determined using inductively coupled plasma-atomic emission spectroscopy (ICPAES). The average metal content of spmoB5 and spmoB7 shown in Table 1 is from 2 and 3 biological replicates (grown and purified independently), respectively. Subsequent activity assays indicate that there is not a direct correlation between metal content and activity.

Methane/Propylene Oxidation Assay Development

Duroquinol was prepared (22; incorporated by reference in its entirety) 20-100 µL of protein was placed in a gas chromatography (GC) vial with ~1-2 mg of solid duroquinol and sealed. Typical protein concentrations were between 5 and 100 µM. 1 mL of propylene, methane or $^{13}C$ labeled methane was added using a syringe. Reactions were then incubated in a shaking water bath set at 20 to 45° C. After 1 to 24 hour(s), samples were moved to −20° C. for about 10 minutes. 500 µl of chloroform was added to samples containing propylene, shaken at 1800 RPM for 10 minutes, and centrifuged at 2,000×g for 2 minutes. The chloroform layer was then chromatographed with an Agilent 7890B gas chromatograph coupled to a 5977A MSD equipped with a 25 m×0.25 mm PorabondQ with particle traps. Single ion mode was used to quantitate the concentration of propylene oxide by monitoring the 58 m/z ion. Methylene chloride was used as an internal standard by monitoring the 49 m/z ion.

For samples containing methane, 500 µL of chloroform was added to each sample and shaken at 1800 RPM for 10 minutes. The samples were then centrifuged at 2,000×g for 2 minutes to clarify the emulsion. The chloroform layer was then transferred to a fresh vial and chromatographed as described above except that the 31 m/z ion and 33 m/z ion was used to quantitate the concentration of methanol and $^{13}C$ labeled methane. The rate of methane oxidation is calculated after correcting for background methanol.

Combination of Mutations from Top Performing Hits

Figure 7:
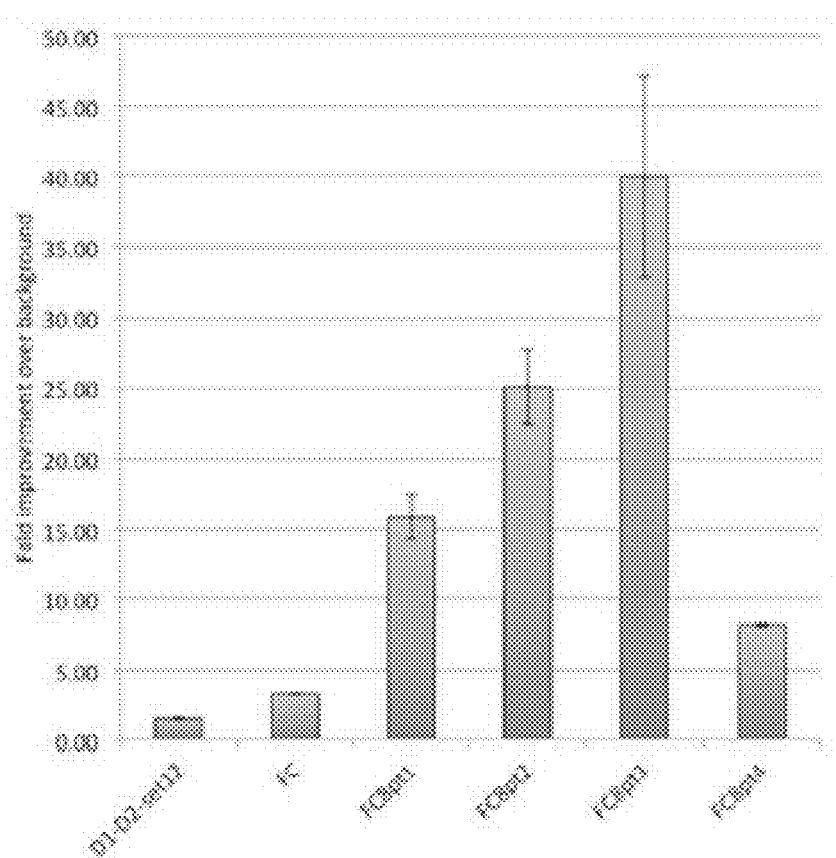
FIG. 7. Improvement in soluble expression of combinatorial mutants of spmoB. All of the combinatorial mutants shown here were built using D1-D2-set12, as in the library screening experiments.
Figure 8:
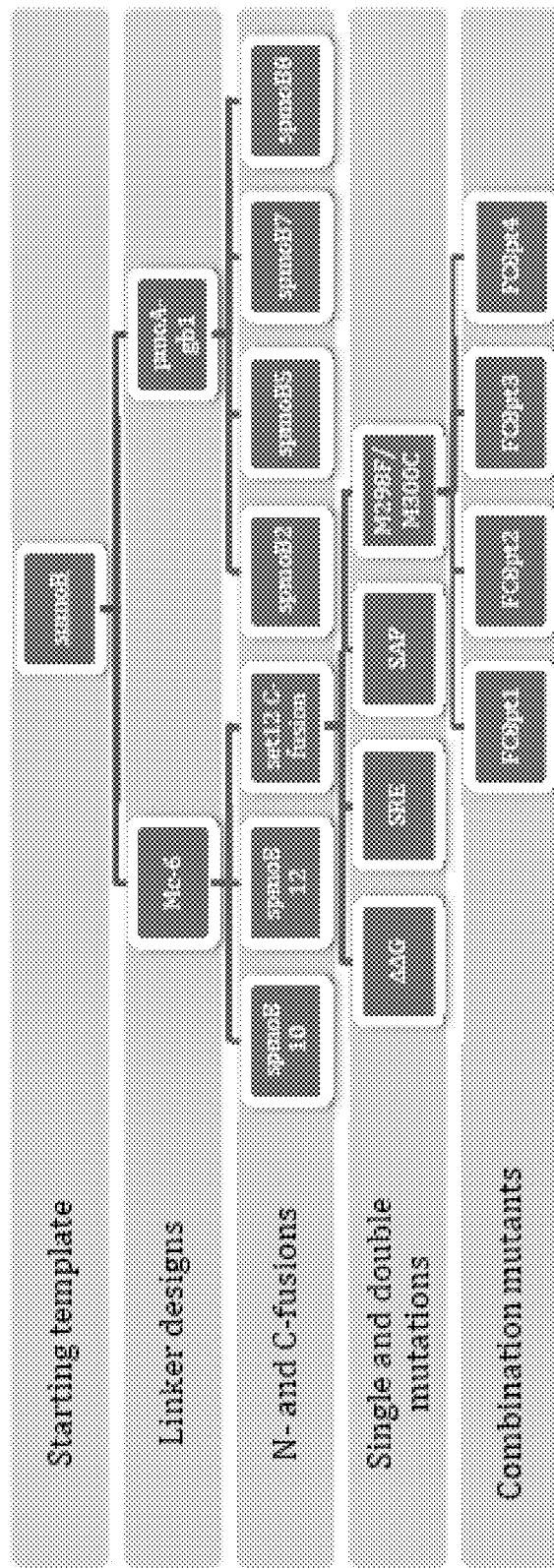
FIG. 8. Ancestry of variants by round of engineering. The starting template is spmoB. Combination mutants FC8pt1-4 are descended from a variant of spmoB with the Mc-6 linker, set12 C-terminal domain fusion, and M298F/M300C base double mutation.

The best single and double mutations obtained from the first round of design (K36Q/V, T80E, P96G/A, G146D/G148L, V293A, M298F/M300C, I380A/Y381E) were combined into the backbone of the screening construct D1-D2-set12. As shown in FIG. 7, these mutations all increase the solubility of the D1-D2-set12 construct to varying degrees and show a similar fold improvement when compared to the multi-domain fusions in FIG. 5 and FIG. 6. The starting backbone was first mutated to include M298F/M300C, generating the FC construct, while the subsequent FC8pt mutations incorporated the following base mutations (T80E, G146D, G148L, V293A, I380A, Y381E), but differed in the combinations at K36Q/V and P96G/A (FC8pt1 K36Q/P96G, FC8pt2 K36Q/P96A, FC8pt3 K36V/P96G, FC8pt4 K36V/

P96A). The best expressing variant based on the GFP assay was FC8pt3. Mutations in variant FC8pt3 were combined with sumo-SpmoB7 to generate sumo-SpmoB7 8pt3, which was capable of oxidizing $^{13}C$ labeled methane to $^{13}C$ methanol.

The number of positions considered presents numerous combinations for consideration when combining variants. Although all of the mutations in the FC8pt series are beneficial, we identified a smaller subset of mutations that provide similar levels of soluble expression. Additional variants include SS1 (K36V, P96G, G146D, M298F, M300C), SS2 (P96G, G146D, M298F, M300C) and the corresponding N-terminal sumo fusions.

Assessment of the Stability and Solubility of Best Variants

Variants of spmoB with increased solubility were expressed and purified to homogeneity using Streptactin resin followed by size exclusion chromatography using a Superdex 75 10/300 GL column (GE Healthcare Life Science, Piscataway, N.J.). The purified proteins showed similar secondary structure to refolded spmoB when examined with circular dichroism; however, no discernible melting transition was observed for any of the variants. Thermofluor assays (ref. 23; incorporated by reference in its entirety) were also performed; however none of the constructs exhibited a thermal transition. It is contemplated that the spmoB proteins exist as a soluble aggregate, which can still allow for significant activity despite having non-traditional tertiary structure (ref. 24; incorporated by reference in its entirety); although the present invention is not limited to any particular mechanism of action and an understanding of the mechanism of action is not necessary to practice the present invention.

Soluble spmoB Variants in Eukaryotic Expression Systems

To test the transferability of the soluble spmoB protein variants, a sampling of early hits from the fusion domain studies were cloned into a *Pichia pastoris*-compatible vector (ref. 25; incorporated by reference in its entirety) The variants were cloned in frame with the alpha mating factor secretion signal, ensuring secretion of the protein out of the cell and into the media. Despite potential difficulties not accounted for during solubility engineering, such as glycosylation, measurable amounts of protein was recovered for one of the variants tested. This shows for the first time the expression of the spmoB protein solubly by a eukaryotic microbe and secreted into the medium.

Similarly, soluble spmoB variants were cloned into the *Saccharomyces cerevisiae* plasmid pPNL6, in frame with the yeast surface protein aga2 to promote yeast display (ref. 26; incorporated by reference in its entirety). Under control of the galactose promoter, spmoB variants were successfully displayed on the surface of yeast as measured by flow cytometry. Roughly 40% of cells counted were fluorescent in response to labeling with an anti-cmyc primary antibody and an anti-IgG secondary antibody conjugated to phycoerythrin.

SEQUENCES

In some embodiments, sequences include a C-terminal TGS tag.
spmoB-C-set12 (SEQ ID NO: 10)
```
MHGEKSQAAFMRMRTIHWYDLSWSKEKVKINETVEIKGKFHVFEGWPETVDEPDVAFL
NVGMPGPVFIRKESYIGGQLVPRSVRLEIGKTYDFRVVLKARRPGDWHVHTMMNVQG
GGPIIGPGKWITVEGSMSEFRNGEPSGEPSGTMRGMKPLELPAPTVSVKVEDATYRVPG
RAMRMKLTITNHGNSPIRLGEFYTASVRFLDSDVYKDTTGYPEDLLAEDGLSVSDNSPL
APGETRTVDVTASDAAWEVYRLSDIIYDPDSRFAGLLFFFDATGNRQVVQIDAPLIPSFM
ENLYFQGGEEASVTSTEETLTPAQEAAETEAANKARKEAELEAETAEQGSGGGSTSRDH
MVLHEYVNAAGITGGGSAWSHPQFEK
``` spmoB2 (D1-pmoA-gb1-D2-set12)(SEQ ID NO: 11)
```
MHGEKSQAAFMRMRTIHWYDLSWSKEKVKINETVEIKGKFHVFEGWPETVDEPDVAFL
NVGMPGPVFIRKESYIGGQLVPRSVRLEIGKTYDFRVVLKARRPGDWHVHTMMNVQG
GGPIIGPGKWITVEGSMSEFRNPVTTLTGQTVDLENGEPSTYKLILNGKTLKGETTTEAV
DAATAEKVFKQYANDNGVDGEWTYDDATKTFTVTEGEPVEYNGMLMSIADIQGYNYV
RTGTPEYIRMVEKGSGTMRGMKPLELPAPTVSVKVEDATYRVPGRAMRMKLTITNHGN
SPIRLGEFYTASVRFLDSDVYKDTTGYPEDLLAEDGLSVSDNSPLAPGETRTVDVTASDA
AWEVYRLSDIIYDPDSRFAGLLFFFDATGNRQVVQIDAPLIPSFMENLYFQGGEEASVTS
TEETLTPAQEAAETEAANKARKEAELEAETAEQGSGGGSTSRDHMVLHEYVNAAGITG
GGSAWSHPQFEK
``` spmoB5 (mbp-D1-pmoA-gb1-D2-set12)(SEQ ID NO: 12)
```
MKIEEGKLVIWINGDKGYNGLAEVGKKFEKDTGIKVTVEHPDKLEEKFPQVAATGDGP
DIIFWAHDRFGGYAQSGLLAEITPDKAFQDKLYPFTWDAVRYNGKLIAYPIAVEALSLIY
NKDLLPNPPKTWEEIPALDKELKAKGKSALMFNLQEPYFTWPLIAADGGYAFKYENGK
YDIKDVGVDNAGAKAGLTFLVDLIKNKHMNADTDYSIAEAAFNKGETAMTINGPWAW
SNIDTSKVNYGVTVLPTFKGQPSKPFVGVLSAGINAASPNKELAKEFLENYLLTDEGLEA
VNKDKPLGAVALKSYEEELVKDPRIAATMENAQKGEIMPNIPQMSAFWYAVRTAVINA
ASGRQTVDEALKDAQTNENLYFQGHGEKSQAAFMRMRTIHWYDLSWSKEKVKINETV
EIKGKFHVFEGWPETVDEPDVAFLNVGMPGPVFIRKESYIGGQLVPRSVRLEIGKTYDFR
VVLKARRPGDWHVHTMMNVQGGGPIIGPGKWITVEGSMSEFRNPVTTLTGQTVDLENG
EPSTYKLILNGKTLKGETTTEAVDAATAEKVFKQYANDNGVDGEWTYDDATKTFTVTE
GEPVEYNGMLMSIADIQGYNYVRTGTPEYIRMVEKGSGTMRGMKPLELPAPTVSVKVE
DATYRVPGRAMRMKLTITNHGNSPIRLGEFYTASVRFLDSDVYKDTTGYPEDLLAEDGL
SVSDNSPLAPGETRTVDVTASDAAWEVYRLSDIIYDPDSRFAGLLFFFDATGNRQVVQID
APLIPSFMENLYFQGGEEASVTSTEETLTPAQEAAETEAANKARKEAELEAETAEQGSGG
GSTSRDHMVLHEYVNAAGITGGGSAWSHPQFEK
``` spmoB7 (set12-D1-pmoA-gb1-D2-set12)(SEQ ID NO: 13)
```
MEEASVTSTEETLTPAQEAAETEAANKARKEAELEAETAEQENLYFQGHGEKSQAAFM
RMRTIHWYDLSWSKEKVKINETVEIKGKFHVFEGWPETVDEPDVAFLNVGMPGPVFIRK
ESYIGGQLVPRSVRLEIGKTYDFRVVLKARRPGDWHVHTMMNVQGGGPIIGPGKWITVE
GSMSEFRNPVTTLTGQTVDLENGEPSTYKLILNGKTLKGETTTEAVDAATAEKVFKQYA
```

| SEQUENCES |
|---|
| NDNGVDGEWTYDDATKTFTVTEGEPVEYNGMLMSIADIQGYNYVRTGTPEYIRMVEK<br>GSGTMRGMKPLELPAPTVSVKVEDATYRVPGRAMIRMKLTITNHGNSPIRLGEFYTASV<br>RFLDSDVYKDTTGYPEDLLAEDGLSVSDNSPLAPGETRTVDVTASDAAWEVYRLSDIIY<br>DPDSRFAGLLFFFDATGNRQVVQIDAPLIPSFMENLYFQGGEEASVTSTEETLTPAQEAA<br>ETEAANKARKEAELEAETAEQGSGGGSTSRDHMVLHEYVNAAGITGGGSAWSHPQFEK<br><br>sumo-spmoB7 (set12-sumo-D1-pmoA-gb1-D2-set12)(SEQ ID NO: 14)<br>MEEASVTSTEETLTPAQEAAETEAANKARKEAELEAETAEQENLYFQGLQDSEVNQEA<br>KPEVKPEVKPETHINLKVSDGSSEIFFKIKKTTPLRRLMEAFAKRQGKEMDSLRFLYDGI<br>RIQADQAPEDLDMEDNDBEAHREQIGGHGEKSQAAFMRMRTIHWYDLSWSKEKVKIN<br>ETVEIKGKFHVFEGWPETVDEPDVAFLNVGMPGPVFIRKESYIGGQLVPRSVRLEIGKTY<br>DFRVVLKARRPGDWHVHTMMNVQGGGPIIGPGKWITVEGSMSEFRNPVTTLTGQTVDL<br>ENGEPSTYKLILNGKTLKGETTTEAVDAATAEKVFKQYANDNGVDGEWTYDDATKTFT<br>VTEGEPVEYNGMLMSIADIQGYNYVRTGTPEYIRMVEKGSGTMRGMKPLELPAPTVSV<br>KVEDATYRVPGRAMRMKLTITNHGNSPIRLGEFYTASVRFLDSDVYKDTTGYPEDLLAE<br>DGLSVSDNSPLAPGETRTVDVTASDAAWEVYRLSDIIYDPDSRFAGLLFFFDATGNRQV<br>VQIDAPLIPSFMENLYFQGGEEASVTSTEETLTPAQEAAETEAANKARKEAELEAETAEQ<br>GSGGGSTSRDHMVLHEYVNAAGITGGGSAWSHPQFEK<br><br>sumo-spmoB7 FC8pt3 (SEQ ID NO: 15)<br>MEIASVTSTEETLTPAQEAAETEAANKARKEAELEAETAEQENLYFQGLQDSEVNQEA<br>KPEVKPEVKPETHINLKVSDGSSEIFFKIKKTTPLRKLMEAFAKRQGKEMDSLRFLYDGI<br>RIQADQAPEDLDMEDNDIIEAHREQIGGHGEVSQAAFMRMRTIHWYDLSWSKEKVKIN<br>ETVEIKGKFHVFEGWPEEVDEPDVAFLNVGMPGPVFIRKESYIGGQLVPRSVRLEIGKTY<br>DFRVVLKARRPGDWHVHTMMNVQDGLPIIGPGKWITVEGSMSEFRNPVTTLTGQTVDL<br>ENGEPSTYKLILNGKTLKGETTTEAVDAATAEKVFKQYANDNGVDGEWTYDDATKTFT<br>VTEGEPVEYNGMLMSIADIQGYNYVRTGTPEYIRMVEKGSGTMRGMKPLELPAPTVSV<br>KVEDATYRAPGRAFRCKLTITNHGNSPIRLGEFYTASVRFLDSDVYKDTTGYPEDLLAE<br>DGLSVSDNSPLAPGETRTVDVTASDAAWEVYRLSDIAEDPDSRFAGLLFFTDATGNRQV<br>VQIDAPLIPSFMENLYFQGGEEASVTSTEETLTPAQEAAETEAANKARKEAELEAETAEQ<br>GSGGGSTSRDHMVLHEYVNAAGITGGGSNWSHPQFEK<br><br>set12 (SEQ ID NO: 16)<br>EEASVTSTEETLTPAQEAAETEAANKARKEAELEAETAEQ<br><br>ENLYFQG (SEQ ID NO: 17)<br>ENLYFQG<br><br>sumo (SEQ ID NO: 18)<br>LQDSEVNQEAKPEVKPEVKPETHINLKVSDGSSEIFFKIKKTTPLRRLMEAFAKRQGKEM<br>DSLRFLYDGIRIQADQAPEDLDMEDNDIIEAHREQIGG<br><br>pmoA-gb1-D2 (SEQ ID NO: 19)<br>PVTTLTGQTVDLENGEPSTYKLILNGKTLKGETTTEAVDAATAEKVFKQYANDNGVDG<br>EWTYDDATKTFTVTEGEPVEYNGMLMSIADIQGYNYVRTGTPEYIRMVEKGSGTMRG<br>MKPLELPAPTVSVKVEDATYRVPGRAMRMKLTITNHGNSPIRLGEFYTASVRFLDSDVY<br>KDTTGYPEDLLAEDGLSVSDNSPLAPGETRTVDVTASDAAWEVYRLSDIIYDPDSRFAG<br>LLFFFDATGNRQVVQIDAPLIPSFMENLYFQGG<br><br>D1 (SEQ ID NO: 20)<br>HGEKSQAAFMRMRTIHWYDLSWSKEKVKINETVEIKGKFHVFEGWPETVDEPDVAFLN<br>VGMPGPVFIRKESYIGGQLVPRSVRLEIGKTYDFRVVLKARRPGDWHVHTMMNVQGG<br>GPIIGPGKWITVEGSMSEFRN<br><br>TGS(SEQ ID NO: 21)<br>GSGGGSTSRDHMVLHEYVNAAGITGGGSAWSHPQFEK<br><br>Mbp (SEQ ID NO: 22)<br>MKIEEGKLVIWINGDKGYNGLQSGLLAEITPDKAKDTGIKVTVEHPDKLEEKFPQVAAT<br>GDGPDIIFWAHDRFGGYAQSGLLAEITPDKAFQDKLYPFTWDAVRYNGKLIAYPIAVEA<br>LSLIYNKDLLPNPPKTWEEIPALDKELKAKGKSALMFNLQEPYFTWPLIAADGGYAFKY<br>ENGKYDIKDVGVDNAGAKAGLTFLVDLIKNKHMNADTDYSIAEAAFNKGETAMTINGP<br>WAWSNIDTSKVNYGVTVLPTFKGQPSKPFVGVLSAGINAASPNKELAKEFLENYLLTDE<br>GLEAVNKDKPLGAVALKSYEEELVKDPRIAATMENAQKGEIMPNIPQMSAFWYAVRTA<br>VINAASGRQTVDEALKDAQTNENLYFQG<br><br>D1-pmoA-gb1-D2 (SEQ ID NO: 23)<br>HGEKSQAAFMRMRTIHWYDLSWSKEKVKINETVEIKGKFHVFEGWPETVDEPDVAFLN<br>VGMPGPVFIRKESYIGGQLVPRSVRLEIGKTYDFRVVLKARRPGDWHVHTMMNVQGG<br>GPIIGPGKWITVEGSMSEFRNPVTTLTGQTVDLENGEPSTYKLILNGKTLKGETTTEAVD<br>AATAEKVFKQYANDNGVDGEWTYDDATKTFTVTEGEPVEYNGMLMSIADIQGYNYVR<br>TGTPEYIRMVEKGSGTMRGMKPLELPAPTVSVKVEDATYRVPGRAMRMKLTITNHGNS<br>PIRLGEFYTASVRFLDSDVYKDTTGYPEDLLAEDGLSVSDNSPLAPGETRTVDVTASDA<br>AWEVYRLSDIIYDPDSRFAGLLFFFDATGNRQVVQIDAPLIPSFMENLYFQGG |

REFERENCES

The following references, many of which are referenced above by number, are herein incorporated by reference in their entireties.
1. Conrado, R. J. and R. Gonzalez, Chemistry. Envisioning the bioconversion of methane to liquid fuels. Science, 2014. 343(6171): p. 621-3.
2. Haynes, C. A. and R. Gonzalez, Rethinking biological activation of methane and conversion to liquid fuels. Nat Chem Biol, 2014. 10(5): p. 331-9.
3. Kjellstrom, T., et al., Public health impact of global heating due to climate change: potential effects on chronic non-communicable diseases. Int J Public Health, 2010. 55(2): p. 97-103.
4. Trotsenko, Y. A. and J. C. Murrell, Metabolic aspects of aerobic obligate methanotrophy, in Adv Appl Microbiol, A. L. Laskin and S. Sariaslani, Editors. 2008, Elsevier Academic Press Inc: San Diego. p. 183-229.
5. Balasubramanian, R., et al., Oxidation of methane by a biological dicopper centre. Nature, 2010. 465: p. 115-119.
6. Tinberg, C. E. and S. J. Lippard, Dioxygen activation in soluble methane monooxygenase. Accounts Chem Res., 2011. 44: p. 280-288.
7. Lieberman, R. L. and A. C. Rosenzweig, Crystal structure of a membrane-bound metalloenzyme that catalyses the biological oxidation of methane. Nature, 2005. 434 (7030): p. 177-82.
8. Smith, S. M., et al., Crystal structure and characterization of particulate methane monooxygenase from *Methylocystis* species strain M. Biochemistry, 2011. 50(47): p. 10231-40.
9. Canutescu, A. A. and R. L. Dunbrack, Jr., Cyclic coordinate descent: A robotics algorithm for protein loop closure. Protein Sci, 2003. 12(5): p. 963-72.
10. Bao, W. J., et al., Highly efficient expression and purification system of small-size protein domains in *Escherichia coli* for biochemical characterization. Protein Expr Purif, 2006. 47(2): p. 599-606.
11. Gastinel, L. N., N. E. Simister, and P. J. Bjorkman, Expression and crystallization of a soluble and functional form of an Fc receptor related to class I histocompatibility molecules. Proc Natl Acad Sci USA, 1992. 89(2): p. 638-42.
12. Correa, A. and P. Oppezzo, Tuning different expression parameters to achieve soluble recombinant proteins in *E. coli*: advantages of high-throughput screening. Biotechnol J, 2011. 6(6): p. 715-30.
13. Taylor, T. J. and Vaisman, I I, Discrimination of thermophilic and mesophilic proteins. BMC Struct Biol, 2010. 10 Suppl 1: p. S5.
14. Guerois, R., J. E. Nielsen, and L. Serrano, Predicting changes in the stability of proteins and protein complexes: A study of more than 1000 mutations. Journal of Molecular Biology, 2002. 320(2): p. 369-387.
15. Rohl, C. A., et al., Protein structure prediction using rosetta. Numerical Computer Methods, Pt D, 2004. 383: p. 66-+.
16. Chica, R. A., et al., Generation of longer emission wavelength red fluorescent proteins using computationally designed libraries. Proc Natl Acad Sci USA, 2010. 107(47): p. 20257-20262.
17. Chennamsetty, N., et al., Prediction of Aggregation Prone Regions of Therapeutic Proteins. Journal of Physical Chemistry B, 2010. 114(19): p. 6614-6624.
18. Gibson, D. G., et al., Enzymatic assembly of DNA molecules up to several hundred kilobases. Nature Methods, 2009. 6(5): p. 343-U41.
19. Cabantous, S. and G. S. Waldo, In vivo and in vitro protein solubility assays using split GFP. Nature Methods, 2006. 3(10): p. 845-854.
20. Skerra, A. and T. G. M. Schmidt, Use of the Strep-tag and streptavidin for detection and purification of recombinant proteins. Applications of Chimeric Genes and Hybrid Proteins, Pt A, 2000. 326: p. 271-304.
21. Unger, T., et al., Applications of the Restriction Free (RF) cloning procedure for molecular manipulations and protein expression. Journal of Structural Biology, 2010. 172(1): p. 34-44.
22. Zahn, J. A. and A. A. DiSpirito, Membrane-associated methane monooxygenase from *Methylococcus capsulatus* (Bath) (vol 178, pg 1018, 1996). Journal of Bacteriology, 1996. 178(9): p. 2726-2726.
23. Phillips, K. and A. H. de la Pena, The combined use of the Thermofluor assay and ThermoQ analytical software for the determination of protein stability and buffer optimization as an aid in protein crystallization. Curr Protoc Mol Biol, 2011. Chapter 10: p. Unit10 28.
24. Garcia-Fruitos, E., et al., Aggregation as bacterial inclusion bodies does not imply inactivation of enzymes and fluorescent proteins. Microb Cell Fact, 2005. 4: p. 27.
25. Lee, C. C., et al., An episomal expression vector for screening mutant gene libraries in *Pichia pastoris*. Plasmid, 2005. 54(1): p. 80-85.
26. Feldhaus, M. J. et al. Flow-cytometric isolation of human antibodies from a nonimmune *Saccharomyces cerevisiae* surface display library. *Nat Biotechnol*, 2003. 21, 163-170.

The invention claimed is:

1. A soluble polypeptide comprising a sequence having at least 80% sequence identity with SEQ ID NO: 13 but less than 100% sequence identity from a naturally-occurring sequence, wherein the soluble polypeptide is capable of converting an alkane into an alkanol.

2. The soluble polypeptide of claim 1, wherein the polypeptide is capable of converting methane into methanol.

3. A method of converting an alkane into an alkanol comprising exposing the alkane to the soluble polypeptide of claim 1.

4. A cell expressing the soluble polypeptide of claim 1.

5. A method of producing a biofuel comprising exposing an alkane to a soluble polypeptide of claim 1.

6. A system comprising a soluble polypeptide of claim 1 attached to a fixed support.

7. The system of claim 6, wherein the fixed support is selected from the list consisting of: a yeast cell, a phage, and a functionalized bead.

8. A bioreactor comprising the soluble polypeptide of claim 1.

9. The bioreactor of claim 8, further comprising methane.

10. The bioreactor of claim 8, further comprising a cell expressing the soluble polypeptide.

* * * * *

SEQUENCE LISTING

```
<160> NUMBER OF SEQ ID NOS: 23

<210> SEQ ID NO 1
<211> LENGTH: 8
<212> TYPE: PRT
<213> ORGANISM: Artificial sequence
<220> FEATURE:
<223> OTHER INFORMATION: Synthetic protein

<400> SEQUENCE: 1

Gly Glu Pro Ser Gly Glu Pro Ser
1               5
```

```
<210> SEQ ID NO 2
<211> LENGTH: 4
<212> TYPE: PRT
<213> ORGANISM: Artificial sequence
<220> FEATURE:
<223> OTHER INFORMATION: Synthetic protein

<400> SEQUENCE: 2

Gly Glu Pro Ser
1

<210> SEQ ID NO 3
<211> LENGTH: 6
<212> TYPE: PRT
<213> ORGANISM: Artificial sequence
<220> FEATURE:
<223> OTHER INFORMATION: Synthetic protein

<400> SEQUENCE: 3

Gly Lys Leu Gly Gly Gly
1               5

<210> SEQ ID NO 4
<211> LENGTH: 5
<212> TYPE: PRT
<213> ORGANISM: Artificial sequence
<220> FEATURE:
<223> OTHER INFORMATION: Synthetic protein

<400> SEQUENCE: 4

Gly Ser Gly Ser Gly
1               5

<210> SEQ ID NO 5
<211> LENGTH: 6
<212> TYPE: PRT
<213> ORGANISM: Artificial sequence
<220> FEATURE:
<223> OTHER INFORMATION: Synthetic protein

<400> SEQUENCE: 5

Gly Ser Gly Ser Gly Ser
1               5

<210> SEQ ID NO 6
<211> LENGTH: 7
<212> TYPE: PRT
<213> ORGANISM: Artificial sequence
<220> FEATURE:
<223> OTHER INFORMATION: Synthetic protein

<400> SEQUENCE: 6

Gly Ser Gly Ser Gly Ser Gly
1               5

<210> SEQ ID NO 7
<211> LENGTH: 8
<212> TYPE: PRT
<213> ORGANISM: Artificial sequence
<220> FEATURE:
<223> OTHER INFORMATION: Synthetic protein

<400> SEQUENCE: 7

Gly Ser Gly Ser Gly Ser Gly Ser
1               5
```

-continued

<210> SEQ ID NO 8
<211> LENGTH: 8
<212> TYPE: PRT
<213> ORGANISM: Artificial sequence
<220> FEATURE:
<223> OTHER INFORMATION: Synthetic protein

<400> SEQUENCE: 8

Gly Ser Gly Glu Pro Ser Gly Ser
1               5

<210> SEQ ID NO 9
<211> LENGTH: 33
<212> TYPE: PRT
<213> ORGANISM: Artificial sequence
<220> FEATURE:
<223> OTHER INFORMATION: Synthetic protein

<400> SEQUENCE: 9

Pro Val Glu Tyr Asn Gly Met Leu Met Ser Ile Ala Asp Ile Gln Gly
1               5                   10                  15

Tyr Asn Tyr Val Arg Thr Gly Thr Pro Glu Tyr Ile Arg Met Val Glu
            20                  25                  30

Lys

<210> SEQ ID NO 10
<211> LENGTH: 378
<212> TYPE: PRT
<213> ORGANISM: Artificial sequence
<220> FEATURE:
<223> OTHER INFORMATION: Synthetic protein

<400> SEQUENCE: 10

Met His Gly Glu Lys Ser Gln Ala Ala Phe Met Arg Met Arg Thr Ile
1               5                   10                  15

His Trp Tyr Asp Leu Ser Trp Ser Lys Glu Lys Val Lys Ile Asn Glu
            20                  25                  30

Thr Val Glu Ile Lys Gly Lys Phe His Val Phe Glu Gly Trp Pro Glu
        35                  40                  45

Thr Val Asp Glu Pro Asp Val Ala Phe Leu Asn Val Gly Met Pro Gly
    50                  55                  60

Pro Val Phe Ile Arg Lys Glu Ser Tyr Ile Gly Gly Gln Leu Val Pro
65                  70                  75                  80

Arg Ser Val Arg Leu Glu Ile Gly Lys Thr Tyr Asp Phe Arg Val Val
                85                  90                  95

Leu Lys Ala Arg Arg Pro Gly Asp Trp His Val His Thr Met Met Asn
            100                 105                 110

Val Gln Gly Gly Gly Pro Ile Ile Gly Pro Gly Lys Trp Ile Thr Val
        115                 120                 125

Glu Gly Ser Met Ser Glu Phe Arg Asn Gly Glu Pro Ser Gly Glu Pro
    130                 135                 140

Ser Gly Thr Met Arg Gly Met Lys Pro Leu Glu Leu Pro Ala Pro Thr
145                 150                 155                 160

Val Ser Val Lys Val Glu Asp Ala Thr Tyr Arg Val Pro Gly Arg Ala
                165                 170                 175

Met Arg Met Lys Leu Thr Ile Thr Asn His Gly Asn Ser Pro Ile Arg
            180                 185                 190

Leu Gly Glu Phe Tyr Thr Ala Ser Val Arg Phe Leu Asp Ser Asp Val
        195                 200                 205

```
Tyr Lys Asp Thr Thr Gly Tyr Pro Glu Asp Leu Leu Ala Glu Asp Gly
    210                 215                 220

Leu Ser Val Ser Asp Asn Ser Pro Leu Ala Pro Gly Glu Thr Arg Thr
225                 230                 235                 240

Val Asp Val Thr Ala Ser Asp Ala Ala Trp Glu Val Tyr Arg Leu Ser
            245                 250                 255

Asp Ile Ile Tyr Asp Pro Asp Ser Arg Phe Ala Gly Leu Leu Phe Phe
                260                 265                 270

Phe Asp Ala Thr Gly Asn Arg Gln Val Val Gln Ile Asp Ala Pro Leu
            275                 280                 285

Ile Pro Ser Phe Met Glu Asn Leu Tyr Phe Gln Gly Gly Glu Ala
    290                 295                 300

Ser Val Thr Ser Thr Glu Glu Thr Leu Thr Pro Ala Gln Glu Ala Ala
305                 310                 315                 320

Glu Thr Glu Ala Ala Asn Lys Ala Arg Lys Glu Ala Glu Leu Glu Ala
                325                 330                 335

Glu Thr Ala Glu Gln Gly Ser Gly Gly Ser Thr Ser Arg Asp His
            340                 345                 350

Met Val Leu His Glu Tyr Val Asn Ala Ala Gly Ile Thr Gly Gly Gly
                355                 360                 365

Ser Ala Trp Ser His Pro Gln Phe Glu Lys
    370                 375

<210> SEQ ID NO 11
<211> LENGTH: 480
<212> TYPE: PRT
<213> ORGANISM: Artificial sequence
<220> FEATURE:
<223> OTHER INFORMATION: Synthetic protein

<400> SEQUENCE: 11

Met His Gly Glu Lys Ser Gln Ala Ala Phe Met Arg Met Arg Thr Ile
1               5                   10                  15

His Trp Tyr Asp Leu Ser Trp Ser Lys Glu Lys Val Lys Ile Asn Glu
                20                  25                  30

Thr Val Glu Ile Lys Gly Lys Phe His Val Phe Glu Gly Trp Pro Glu
            35                  40                  45

Thr Val Asp Glu Pro Asp Val Ala Phe Leu Asn Val Gly Met Pro Gly
        50                  55                  60

Pro Val Phe Ile Arg Lys Glu Ser Tyr Ile Gly Gly Gln Leu Val Pro
65                  70                  75                  80

Arg Ser Val Arg Leu Glu Ile Gly Lys Thr Tyr Asp Phe Arg Val Val
                85                  90                  95

Leu Lys Ala Arg Arg Pro Gly Asp Trp His Val His Thr Met Met Asn
                100                 105                 110

Val Gln Gly Gly Gly Pro Ile Ile Gly Pro Gly Lys Trp Ile Thr Val
            115                 120                 125

Glu Gly Ser Met Ser Glu Phe Arg Asn Pro Val Thr Thr Leu Thr Gly
        130                 135                 140

Gln Thr Val Asp Leu Glu Asn Gly Glu Pro Ser Thr Tyr Lys Leu Ile
145                 150                 155                 160

Leu Asn Gly Lys Thr Leu Lys Gly Glu Thr Thr Thr Glu Ala Val Asp
                165                 170                 175

Ala Ala Thr Ala Glu Lys Val Phe Lys Gln Tyr Ala Asn Asp Asn Gly
            180                 185                 190
```

```
Val Asp Gly Glu Trp Thr Tyr Asp Ala Thr Lys Thr Phe Thr Val
            195                 200                 205

Thr Glu Gly Glu Pro Val Glu Tyr Asn Gly Met Leu Met Ser Ile Ala
    210                 215                 220

Asp Ile Gln Gly Tyr Asn Tyr Val Arg Thr Gly Thr Pro Glu Tyr Ile
225                 230                 235                 240

Arg Met Val Glu Lys Gly Ser Gly Thr Met Arg Gly Met Lys Pro Leu
                245                 250                 255

Glu Leu Pro Ala Pro Thr Val Ser Val Lys Val Glu Asp Ala Thr Tyr
            260                 265                 270

Arg Val Pro Gly Arg Ala Met Arg Met Lys Leu Thr Ile Thr Asn His
        275                 280                 285

Gly Asn Ser Pro Ile Arg Leu Gly Glu Phe Tyr Thr Ala Ser Val Arg
    290                 295                 300

Phe Leu Asp Ser Asp Val Tyr Lys Asp Thr Thr Gly Tyr Pro Glu Asp
305                 310                 315                 320

Leu Leu Ala Glu Asp Gly Leu Ser Val Ser Asp Asn Ser Pro Leu Ala
                325                 330                 335

Pro Gly Glu Thr Arg Thr Val Asp Val Thr Ala Ser Asp Ala Ala Trp
            340                 345                 350

Glu Val Tyr Arg Leu Ser Asp Ile Ile Tyr Asp Pro Asp Ser Arg Phe
        355                 360                 365

Ala Gly Leu Leu Phe Phe Asp Ala Thr Gly Asn Arg Gln Val Val
    370                 375                 380

Gln Ile Asp Ala Pro Leu Ile Pro Ser Phe Met Glu Asn Leu Tyr Phe
385                 390                 395                 400

Gln Gly Gly Glu Glu Ala Ser Val Thr Ser Thr Glu Thr Leu Thr
                405                 410                 415

Pro Ala Gln Glu Ala Ala Glu Thr Glu Ala Ala Asn Lys Ala Arg Lys
            420                 425                 430

Glu Ala Glu Leu Glu Ala Glu Thr Ala Glu Gln Gly Ser Gly Gly
        435                 440                 445

Ser Thr Ser Arg Asp His Met Val Leu His Glu Tyr Val Asn Ala Ala
    450                 455                 460

Gly Ile Thr Gly Gly Gly Ser Ala Trp Ser His Pro Gln Phe Glu Lys
465                 470                 475                 480

<210> SEQ ID NO 12
<211> LENGTH: 854
<212> TYPE: PRT
<213> ORGANISM: Artificial sequence
<220> FEATURE:
<223> OTHER INFORMATION: Synthetic protein

<400> SEQUENCE: 12

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
        50                  55                  60

His Asp Arg Phe Gly Gly Tyr Ala Gln Ser Gly Leu Leu Ala Glu Ile
65                  70                  75                  80
```

```
Thr Pro Asp Lys Ala Phe Gln Asp Lys Leu Tyr Pro Phe Thr Trp Asp
             85                  90                  95
Ala Val Arg Tyr Asn Gly Lys Leu Ile Ala Tyr Pro Ile Ala Val Glu
        100                 105                 110
Ala Leu Ser Leu Ile Tyr Asn Lys Asp Leu Leu Pro Asn Pro Pro Lys
    115                 120                 125
Thr Trp Glu Glu Ile Pro Ala Leu Asp Lys Glu Leu Lys Ala Lys Gly
130                 135                 140
Lys Ser Ala Leu Met Phe Asn Leu Gln Glu Pro Tyr Phe Thr Trp Pro
145                 150                 155                 160
Leu Ile Ala Ala Asp Gly Gly Tyr Ala Phe Lys Tyr Glu Asn Gly Lys
                165                 170                 175
Tyr Asp Ile Lys Asp Val Gly Val Asp Asn Ala Gly Ala Lys Ala Gly
            180                 185                 190
Leu Thr Phe Leu Val Asp Leu Ile Lys Asn Lys His Met Asn Ala Asp
        195                 200                 205
Thr Asp Tyr Ser Ile Ala Glu Ala Ala Phe Asn Lys Gly Glu Thr Ala
    210                 215                 220
Met Thr Ile Asn Gly Pro Trp Ala Trp Ser Asn Ile Asp Thr Ser Lys
225                 230                 235                 240
Val Asn Tyr Gly Val Thr Val Leu Pro Thr Phe Lys Gly Gln Pro Ser
                245                 250                 255
Lys Pro Phe Val Gly Val Leu Ser Ala Gly Ile Asn Ala Ala Ser Pro
            260                 265                 270
Asn Lys Glu Leu Ala Lys Glu Phe Leu Glu Asn Tyr Leu Leu Thr Asp
        275                 280                 285
Glu Gly Leu Glu Ala Val Asn Lys Asp Lys Pro Leu Gly Ala Val Ala
    290                 295                 300
Leu Lys Ser Tyr Glu Glu Leu Val Lys Asp Pro Arg Ile Ala Ala
305                 310                 315                 320
Thr Met Glu Asn Ala Gln Lys Gly Glu Ile Met Pro Asn Ile Pro Gln
                325                 330                 335
Met Ser Ala Phe Trp Tyr Ala Val Arg Thr Ala Val Ile Asn Ala Ala
            340                 345                 350
Ser Gly Arg Gln Thr Val Asp Glu Ala Leu Lys Asp Ala Gln Thr Asn
        355                 360                 365
Glu Asn Leu Tyr Phe Gln Gly His Gly Glu Lys Ser Gln Ala Ala Phe
    370                 375                 380
Met Arg Met Arg Thr Ile His Trp Tyr Asp Leu Ser Trp Ser Lys Glu
385                 390                 395                 400
Lys Val Lys Ile Asn Glu Thr Val Glu Ile Lys Gly Lys Phe His Val
                405                 410                 415
Phe Glu Gly Trp Pro Glu Thr Val Asp Glu Pro Asp Val Ala Phe Leu
            420                 425                 430
Asn Val Gly Met Pro Gly Pro Val Phe Ile Arg Lys Glu Ser Tyr Ile
        435                 440                 445
Gly Gly Gln Leu Val Pro Arg Ser Val Arg Leu Glu Ile Gly Lys Thr
    450                 455                 460
Tyr Asp Phe Arg Val Val Leu Lys Ala Arg Arg Pro Gly Asp Trp His
465                 470                 475                 480
Val His Thr Met Met Asn Val Gln Gly Gly Pro Ile Ile Gly Pro
                485                 490                 495
```

-continued

```
Gly Lys Trp Ile Thr Val Glu Gly Ser Met Ser Glu Phe Arg Asn Pro
                500                 505                 510

Val Thr Thr Leu Thr Gly Gln Thr Val Asp Leu Glu Asn Gly Glu Pro
            515                 520                 525

Ser Thr Tyr Lys Leu Ile Leu Asn Gly Lys Thr Leu Lys Gly Glu Thr
        530                 535                 540

Thr Thr Glu Ala Val Asp Ala Ala Thr Ala Glu Lys Val Phe Lys Gln
545                 550                 555                 560

Tyr Ala Asn Asp Asn Gly Val Asp Gly Glu Trp Thr Tyr Asp Asp Ala
                565                 570                 575

Thr Lys Thr Phe Thr Val Thr Glu Gly Glu Pro Val Glu Tyr Asn Gly
            580                 585                 590

Met Leu Met Ser Ile Ala Asp Ile Gln Gly Tyr Asn Tyr Val Arg Thr
        595                 600                 605

Gly Thr Pro Glu Tyr Ile Arg Met Val Glu Lys Gly Ser Gly Thr Met
                610                 615                 620

Arg Gly Met Lys Pro Leu Glu Leu Pro Ala Pro Thr Val Ser Val Lys
625                 630                 635                 640

Val Glu Asp Ala Thr Tyr Arg Val Pro Gly Arg Ala Met Arg Met Lys
                645                 650                 655

Leu Thr Ile Thr Asn His Gly Asn Ser Pro Ile Arg Leu Gly Glu Phe
            660                 665                 670

Tyr Thr Ala Ser Val Arg Phe Leu Asp Ser Asp Val Tyr Lys Asp Thr
        675                 680                 685

Thr Gly Tyr Pro Glu Asp Leu Leu Ala Glu Asp Gly Leu Ser Val Ser
        690                 695                 700

Asp Asn Ser Pro Leu Ala Pro Gly Glu Thr Arg Thr Val Asp Val Thr
705                 710                 715                 720

Ala Ser Asp Ala Ala Trp Glu Val Tyr Arg Leu Ser Asp Ile Ile Tyr
                725                 730                 735

Asp Pro Asp Ser Arg Phe Ala Gly Leu Leu Phe Phe Phe Asp Ala Thr
            740                 745                 750

Gly Asn Arg Gln Val Val Gln Ile Asp Ala Pro Leu Ile Pro Ser Phe
        755                 760                 765

Met Glu Asn Leu Tyr Phe Gln Gly Gly Glu Glu Ala Ser Val Thr Ser
    770                 775                 780

Thr Glu Glu Thr Leu Thr Pro Ala Gln Glu Ala Ala Glu Thr Glu Ala
785                 790                 795                 800

Ala Asn Lys Ala Arg Lys Glu Ala Glu Leu Glu Ala Glu Thr Ala Glu
                805                 810                 815

Gln Gly Ser Gly Gly Ser Thr Ser Arg Asp His Met Val Leu His
            820                 825                 830

Glu Tyr Val Asn Ala Ala Gly Ile Thr Gly Gly Ser Ala Trp Ser
        835                 840                 845

His Pro Gln Phe Glu Lys
    850
```

<210> SEQ ID NO 13
<211> LENGTH: 527
<212> TYPE: PRT
<213> ORGANISM: Artificial sequence
<220> FEATURE:
<223> OTHER INFORMATION: Synthetic protein

```
<400> SEQUENCE: 13

Met Glu Glu Ala Ser Val Thr Ser Thr Glu Thr Leu Thr Pro Ala
1               5                   10                  15

Gln Glu Ala Ala Glu Thr Glu Ala Ala Asn Lys Ala Arg Lys Glu Ala
            20                  25                  30

Glu Leu Glu Ala Glu Thr Ala Glu Gln Glu Asn Leu Tyr Phe Gln Gly
        35                  40                  45

His Gly Glu Lys Ser Gln Ala Ala Phe Met Arg Met Arg Thr Ile His
    50                  55                  60

Trp Tyr Asp Leu Ser Trp Ser Lys Glu Lys Val Lys Ile Asn Glu Thr
65                  70                  75                  80

Val Glu Ile Lys Gly Lys Phe His Val Phe Glu Gly Trp Pro Glu Thr
                85                  90                  95

Val Asp Glu Pro Asp Val Ala Phe Leu Asn Val Gly Met Pro Gly Pro
            100                 105                 110

Val Phe Ile Arg Lys Glu Ser Tyr Ile Gly Gly Gln Leu Val Pro Arg
        115                 120                 125

Ser Val Arg Leu Glu Ile Gly Lys Thr Tyr Asp Phe Arg Val Val Leu
    130                 135                 140

Lys Ala Arg Arg Pro Gly Asp Trp His Val His Thr Met Met Asn Val
145                 150                 155                 160

Gln Gly Gly Gly Pro Ile Ile Gly Pro Gly Lys Trp Ile Thr Val Glu
                165                 170                 175

Gly Ser Met Ser Glu Phe Arg Asn Pro Val Thr Thr Leu Thr Gly Gln
            180                 185                 190

Thr Val Asp Leu Glu Asn Gly Glu Pro Ser Thr Tyr Lys Leu Ile Leu
        195                 200                 205

Asn Gly Lys Thr Leu Lys Gly Thr Thr Thr Glu Ala Val Asp Ala
    210                 215                 220

Ala Thr Ala Glu Lys Val Phe Lys Gln Tyr Ala Asn Asp Asn Gly Val
225                 230                 235                 240

Asp Gly Glu Trp Thr Tyr Asp Asp Ala Thr Lys Thr Phe Thr Val Thr
                245                 250                 255

Glu Gly Glu Pro Val Glu Tyr Asn Gly Met Leu Met Ser Ile Ala Asp
            260                 265                 270

Ile Gln Gly Tyr Asn Tyr Val Arg Thr Gly Thr Pro Glu Tyr Ile Arg
        275                 280                 285

Met Val Glu Lys Gly Ser Gly Thr Met Arg Gly Met Lys Pro Leu Glu
    290                 295                 300

Leu Pro Ala Pro Thr Val Ser Val Lys Val Glu Asp Ala Thr Tyr Arg
305                 310                 315                 320

Val Pro Gly Arg Ala Met Arg Met Lys Leu Thr Ile Thr Asn His Gly
                325                 330                 335

Asn Ser Pro Ile Arg Leu Gly Glu Phe Tyr Thr Ala Ser Val Arg Phe
            340                 345                 350

Leu Asp Ser Asp Val Tyr Lys Asp Thr Thr Gly Tyr Pro Glu Asp Leu
        355                 360                 365

Leu Ala Glu Asp Gly Leu Ser Val Ser Asp Asn Ser Pro Leu Ala Pro
    370                 375                 380

Gly Glu Thr Arg Thr Val Asp Val Thr Ala Ser Asp Ala Ala Trp Glu
385                 390                 395                 400

Val Tyr Arg Leu Ser Asp Ile Ile Tyr Asp Pro Asp Ser Arg Phe Ala
                405                 410                 415
```

```
Gly Leu Leu Phe Phe Asp Ala Thr Gly Asn Arg Gln Val Val Gln
            420                 425                 430

Ile Asp Ala Pro Leu Ile Pro Ser Phe Met Glu Asn Leu Tyr Phe Gln
        435                 440                 445

Gly Gly Glu Glu Ala Ser Val Thr Ser Thr Glu Thr Leu Thr Pro
    450                 455                 460

Ala Gln Glu Ala Ala Glu Thr Glu Ala Ala Asn Lys Ala Arg Lys Glu
465                 470                 475                 480

Ala Glu Leu Glu Ala Glu Thr Ala Glu Gln Gly Ser Gly Gly Ser
                485                 490                 495

Thr Ser Arg Asp His Met Val Leu His Glu Tyr Val Asn Ala Ala Gly
            500                 505                 510

Ile Thr Gly Gly Gly Ser Ala Trp Ser His Pro Gln Phe Glu Lys
        515                 520                 525

<210> SEQ ID NO 14
<211> LENGTH: 625
<212> TYPE: PRT
<213> ORGANISM: Artificial sequence
<220> FEATURE:
<223> OTHER INFORMATION: Synthetic protein

<400> SEQUENCE: 14

Met Glu Glu Ala Ser Val Thr Ser Thr Glu Thr Leu Thr Pro Ala
1               5                   10                  15

Gln Glu Ala Ala Glu Thr Glu Ala Ala Asn Lys Ala Arg Lys Glu Ala
                20                  25                  30

Glu Leu Glu Ala Glu Thr Ala Glu Gln Glu Asn Leu Tyr Phe Gln Gly
            35                  40                  45

Leu Gln Asp Ser Glu Val Asn Gln Glu Ala Lys Pro Glu Val Lys Pro
50                  55                  60

Glu Val Lys Pro Glu Thr His Ile Asn Leu Lys Val Ser Asp Gly Ser
65                  70                  75                  80

Ser Glu Ile Phe Phe Lys Ile Lys Lys Thr Thr Pro Leu Arg Arg Leu
                85                  90                  95

Met Glu Ala Phe Ala Lys Arg Gln Gly Lys Glu Met Asp Ser Leu Arg
            100                 105                 110

Phe Leu Tyr Asp Gly Ile Arg Ile Gln Ala Asp Gln Ala Pro Glu Asp
        115                 120                 125

Leu Asp Met Glu Asp Asn Asp Ile Ile Glu Ala His Arg Glu Gln Ile
    130                 135                 140

Gly Gly His Gly Glu Lys Ser Gln Ala Ala Phe Met Arg Met Arg Thr
145                 150                 155                 160

Ile His Trp Tyr Asp Leu Ser Trp Ser Lys Glu Lys Val Lys Ile Asn
                165                 170                 175

Glu Thr Val Glu Ile Lys Gly Lys Phe His Val Phe Glu Gly Trp Pro
            180                 185                 190

Glu Thr Val Asp Glu Pro Asp Val Ala Phe Leu Asn Val Gly Met Pro
        195                 200                 205

Gly Pro Val Phe Ile Arg Lys Glu Ser Tyr Ile Gly Gly Gln Leu Val
    210                 215                 220

Pro Arg Ser Val Arg Leu Glu Ile Gly Lys Thr Tyr Asp Phe Arg Val
225                 230                 235                 240

Val Leu Lys Ala Arg Arg Pro Gly Asp Trp His Val His Thr Met Met
                245                 250                 255
```

```
Asn Val Gln Gly Gly Pro Ile Ile Gly Pro Gly Lys Trp Ile Thr
                260                 265                 270
Val Glu Gly Ser Met Ser Glu Phe Arg Asn Pro Val Thr Thr Leu Thr
        275                 280                 285
Gly Gln Thr Val Asp Leu Glu Asn Gly Glu Pro Ser Thr Tyr Lys Leu
    290                 295                 300
Ile Leu Asn Gly Lys Thr Leu Lys Gly Glu Thr Thr Thr Glu Ala Val
305                 310                 315                 320
Asp Ala Ala Thr Ala Glu Lys Val Phe Lys Gln Tyr Ala Asn Asp Asn
                325                 330                 335
Gly Val Asp Gly Glu Trp Thr Tyr Asp Asp Ala Thr Lys Thr Phe Thr
            340                 345                 350
Val Thr Glu Gly Glu Pro Val Glu Tyr Asn Gly Met Leu Met Ser Ile
        355                 360                 365
Ala Asp Ile Gln Gly Tyr Asn Tyr Val Arg Thr Gly Thr Pro Glu Tyr
    370                 375                 380
Ile Arg Met Val Glu Lys Gly Ser Gly Thr Met Arg Gly Met Lys Pro
385                 390                 395                 400
Leu Glu Leu Pro Ala Pro Thr Val Ser Val Lys Val Glu Asp Ala Thr
                405                 410                 415
Tyr Arg Val Pro Gly Arg Ala Met Arg Met Lys Leu Thr Ile Thr Asn
            420                 425                 430
His Gly Asn Ser Pro Ile Arg Leu Gly Glu Phe Tyr Thr Ala Ser Val
        435                 440                 445
Arg Phe Leu Asp Ser Asp Val Tyr Lys Asp Thr Thr Gly Tyr Pro Glu
    450                 455                 460
Asp Leu Leu Ala Glu Asp Gly Leu Ser Val Ser Asp Asn Ser Pro Leu
465                 470                 475                 480
Ala Pro Gly Glu Thr Arg Thr Val Asp Val Thr Ala Ser Asp Ala Ala
                485                 490                 495
Trp Glu Val Tyr Arg Leu Ser Asp Ile Ile Tyr Asp Pro Asp Ser Arg
            500                 505                 510
Phe Ala Gly Leu Leu Phe Phe Phe Asp Ala Thr Gly Asn Arg Gln Val
        515                 520                 525
Val Gln Ile Asp Ala Pro Leu Ile Pro Ser Phe Met Glu Asn Leu Tyr
    530                 535                 540
Phe Gln Gly Gly Glu Glu Ala Ser Val Thr Ser Thr Glu Glu Thr Leu
545                 550                 555                 560
Thr Pro Ala Gln Glu Ala Ala Glu Thr Glu Ala Ala Asn Lys Ala Arg
                565                 570                 575
Lys Glu Ala Glu Leu Glu Ala Glu Thr Ala Glu Gln Gly Ser Gly Gly
            580                 585                 590
Gly Ser Thr Ser Arg Asp His Met Val Leu His Glu Tyr Val Asn Ala
        595                 600                 605
Ala Gly Ile Thr Gly Gly Gly Ser Ala Trp Ser His Pro Gln Phe Glu
    610                 615                 620
Lys
625

<210> SEQ ID NO 15
<211> LENGTH: 625
<212> TYPE: PRT
<213> ORGANISM: Artificial sequence
<220> FEATURE:
<223> OTHER INFORMATION: Synthetic protein
```

```
<400> SEQUENCE: 15

Met Glu Glu Ala Ser Val Thr Ser Thr Glu Thr Leu Thr Pro Ala
1               5                   10                  15

Gln Glu Ala Ala Glu Thr Glu Ala Ala Asn Lys Ala Arg Lys Glu Ala
            20                  25                  30

Glu Leu Glu Ala Glu Thr Ala Glu Gln Glu Asn Leu Tyr Phe Gln Gly
            35                  40                  45

Leu Gln Asp Ser Glu Val Asn Gln Glu Ala Lys Pro Glu Val Lys Pro
    50                  55                  60

Glu Val Lys Pro Glu Thr His Ile Asn Leu Lys Val Ser Asp Gly Ser
65                  70                  75                  80

Ser Glu Ile Phe Phe Lys Ile Lys Lys Thr Thr Pro Leu Arg Arg Leu
                85                  90                  95

Met Glu Ala Phe Ala Lys Arg Gln Gly Lys Glu Met Asp Ser Leu Arg
            100                 105                 110

Phe Leu Tyr Asp Gly Ile Arg Ile Gln Ala Asp Gln Ala Pro Glu Asp
        115                 120                 125

Leu Asp Met Glu Asp Asn Asp Ile Ile Glu Ala His Arg Glu Gln Ile
    130                 135                 140

Gly Gly His Gly Glu Val Ser Gln Ala Ala Phe Met Arg Met Arg Thr
145                 150                 155                 160

Ile His Trp Tyr Asp Leu Ser Trp Ser Lys Glu Lys Val Lys Ile Asn
                165                 170                 175

Glu Thr Val Glu Ile Lys Gly Lys Phe His Val Phe Glu Gly Trp Pro
            180                 185                 190

Glu Glu Val Asp Glu Pro Asp Val Ala Phe Leu Asn Val Gly Met Pro
        195                 200                 205

Gly Gly Val Phe Ile Arg Lys Glu Ser Tyr Ile Gly Gly Gln Leu Val
    210                 215                 220

Pro Arg Ser Val Arg Leu Glu Ile Gly Lys Thr Tyr Asp Phe Arg Val
225                 230                 235                 240

Val Leu Lys Ala Arg Arg Pro Gly Asp Trp His Val His Thr Met Met
                245                 250                 255

Asn Val Gln Asp Gly Leu Pro Ile Ile Gly Pro Gly Lys Trp Ile Thr
            260                 265                 270

Val Glu Gly Ser Met Ser Glu Phe Arg Asn Pro Val Thr Thr Leu Thr
        275                 280                 285

Gly Gln Thr Val Asp Leu Glu Asn Gly Glu Pro Ser Thr Tyr Lys Leu
    290                 295                 300

Ile Leu Asn Gly Lys Thr Leu Lys Gly Glu Thr Thr Glu Ala Val
305                 310                 315                 320

Asp Ala Ala Thr Ala Glu Lys Val Phe Lys Gln Tyr Ala Asn Asp Asn
                325                 330                 335

Gly Val Asp Gly Glu Trp Thr Tyr Asp Asp Ala Thr Lys Thr Phe Thr
            340                 345                 350

Val Thr Glu Gly Glu Pro Val Glu Tyr Asn Gly Met Leu Met Ser Ile
        355                 360                 365

Ala Asp Ile Gln Gly Tyr Asn Tyr Val Arg Thr Gly Thr Pro Glu Tyr
    370                 375                 380

Ile Arg Met Val Glu Lys Gly Ser Gly Thr Met Arg Gly Met Lys Pro
385                 390                 395                 400

Leu Glu Leu Pro Ala Pro Thr Val Ser Val Lys Val Glu Asp Ala Thr
                405                 410                 415
```

```
Tyr Arg Ala Pro Gly Arg Ala Phe Arg Cys Lys Leu Thr Ile Thr Asn
            420                 425                 430

His Gly Asn Ser Pro Ile Arg Leu Gly Glu Phe Tyr Thr Ala Ser Val
            435                 440                 445

Arg Phe Leu Asp Ser Asp Val Tyr Lys Asp Thr Thr Gly Tyr Pro Glu
        450                 455                 460

Asp Leu Leu Ala Glu Asp Gly Leu Ser Val Ser Asp Asn Ser Pro Leu
465                 470                 475                 480

Ala Pro Gly Glu Thr Arg Thr Val Asp Val Thr Ala Ser Asp Ala Ala
                    485                 490                 495

Trp Glu Val Tyr Arg Leu Ser Asp Ile Ala Glu Asp Pro Asp Ser Arg
                500                 505                 510

Phe Ala Gly Leu Leu Phe Phe Phe Asp Ala Thr Gly Asn Arg Gln Val
                515                 520                 525

Val Gln Ile Asp Ala Pro Leu Ile Pro Ser Phe Met Glu Asn Leu Tyr
                530                 535                 540

Phe Gln Gly Gly Glu Glu Ala Ser Val Thr Ser Thr Glu Glu Thr Leu
545                 550                 555                 560

Thr Pro Ala Gln Glu Ala Ala Glu Thr Glu Ala Ala Asn Lys Ala Arg
                565                 570                 575

Lys Glu Ala Glu Leu Glu Ala Glu Thr Ala Glu Gln Gly Ser Gly Gly
                580                 585                 590

Gly Ser Thr Ser Arg Asp His Met Val Leu His Glu Tyr Val Asn Ala
                595                 600                 605

Ala Gly Ile Thr Gly Gly Gly Ser Ala Trp Ser His Pro Gln Phe Glu
            610                 615                 620

Lys
625

<210> SEQ ID NO 16
<211> LENGTH: 40
<212> TYPE: PRT
<213> ORGANISM: Artificial sequence
<220> FEATURE:
<223> OTHER INFORMATION: Synthetic protein

<400> SEQUENCE: 16

Glu Glu Ala Ser Val Thr Ser Thr Glu Glu Thr Leu Thr Pro Ala Gln
1               5                   10                  15

Glu Ala Ala Glu Thr Glu Ala Ala Asn Lys Ala Arg Lys Glu Ala Glu
            20                  25                  30

Leu Glu Ala Glu Thr Ala Glu Gln
        35                  40

<210> SEQ ID NO 17
<211> LENGTH: 7
<212> TYPE: PRT
<213> ORGANISM: Artificial sequence
<220> FEATURE:
<223> OTHER INFORMATION: Synthetic protein

<400> SEQUENCE: 17

Glu Asn Leu Tyr Phe Gln Gly
1               5

<210> SEQ ID NO 18
<211> LENGTH: 98
<212> TYPE: PRT
<213> ORGANISM: Artificial sequence
```

```
<220> FEATURE:
<223> OTHER INFORMATION: Synthetic protein

<400> SEQUENCE: 18

Leu Gln Asp Ser Glu Val Asn Gln Glu Ala Lys Pro Glu Val Lys Pro
1               5                   10                  15

Glu Val Lys Pro Glu Thr His Ile Asn Leu Lys Val Ser Asp Gly Ser
            20                  25                  30

Ser Glu Ile Phe Phe Lys Ile Lys Lys Thr Thr Pro Leu Arg Arg Leu
        35                  40                  45

Met Glu Ala Phe Ala Lys Arg Gln Gly Lys Glu Met Asp Ser Leu Arg
    50                  55                  60

Phe Leu Tyr Asp Gly Ile Arg Ile Gln Ala Asp Gln Ala Pro Glu Asp
65                  70                  75                  80

Leu Asp Met Glu Asp Asn Asp Ile Ile Glu Ala His Arg Glu Gln Ile
                85                  90                  95

Gly Gly

<210> SEQ ID NO 19
<211> LENGTH: 266
<212> TYPE: PRT
<213> ORGANISM: Artificial sequence
<220> FEATURE:
<223> OTHER INFORMATION: Synthetic protein

<400> SEQUENCE: 19

Pro Val Thr Thr Leu Thr Gly Gln Thr Val Asp Leu Glu Asn Gly Glu
1               5                   10                  15

Pro Ser Thr Tyr Lys Leu Ile Leu Asn Gly Lys Thr Leu Lys Gly Glu
            20                  25                  30

Thr Thr Thr Glu Ala Val Asp Ala Ala Thr Ala Glu Lys Val Phe Lys
        35                  40                  45

Gln Tyr Ala Asn Asp Asn Gly Val Asp Gly Glu Trp Thr Tyr Asp Asp
    50                  55                  60

Ala Thr Lys Thr Phe Thr Val Thr Glu Gly Pro Val Glu Tyr Asn
65                  70                  75                  80

Gly Met Leu Met Ser Ile Ala Asp Ile Gln Gly Tyr Asn Tyr Val Arg
                85                  90                  95

Thr Gly Thr Pro Glu Tyr Ile Arg Met Val Lys Ser Gly Thr
            100                 105                 110

Met Arg Gly Met Lys Pro Leu Glu Leu Pro Ala Pro Thr Val Ser Val
            115                 120                 125

Lys Val Glu Asp Ala Thr Tyr Arg Val Pro Gly Arg Ala Met Arg Met
        130                 135                 140

Lys Leu Thr Ile Thr Asn His Gly Asn Ser Pro Ile Arg Leu Gly Glu
145                 150                 155                 160

Phe Tyr Thr Ala Ser Val Arg Phe Leu Asp Ser Asp Val Tyr Lys Asp
                165                 170                 175

Thr Thr Gly Tyr Pro Glu Asp Leu Leu Ala Glu Asp Gly Leu Ser Val
            180                 185                 190

Ser Asp Asn Ser Pro Leu Ala Pro Gly Glu Thr Arg Thr Val Asp Val
        195                 200                 205

Thr Ala Ser Asp Ala Ala Trp Glu Val Tyr Arg Leu Ser Asp Ile Ile
    210                 215                 220

Tyr Asp Pro Asp Ser Arg Phe Ala Gly Leu Leu Phe Phe Phe Asp Ala
225                 230                 235                 240
```

```
Thr Gly Asn Arg Gln Val Val Gln Ile Asp Ala Pro Leu Ile Pro Ser
            245                 250                 255

Phe Met Glu Asn Leu Tyr Phe Gln Gly Gly
        260                 265

<210> SEQ ID NO 20
<211> LENGTH: 136
<212> TYPE: PRT
<213> ORGANISM: Artificial sequence
<220> FEATURE:
<223> OTHER INFORMATION: Synthetic protein

<400> SEQUENCE: 20

His Gly Glu Lys Ser Gln Ala Ala Phe Met Arg Met Arg Thr Ile His
1               5                   10                  15

Trp Tyr Asp Leu Ser Trp Ser Lys Glu Lys Val Lys Ile Asn Glu Thr
            20                  25                  30

Val Glu Ile Lys Gly Lys Phe His Val Phe Glu Gly Trp Pro Glu Thr
        35                  40                  45

Val Asp Glu Pro Asp Val Ala Phe Leu Asn Val Gly Met Pro Gly Pro
    50                  55                  60

Val Phe Ile Arg Lys Glu Ser Tyr Ile Gly Gly Gln Leu Val Pro Arg
65                  70                  75                  80

Ser Val Arg Leu Glu Ile Gly Lys Thr Tyr Asp Phe Arg Val Val Leu
                85                  90                  95

Lys Ala Arg Arg Pro Gly Asp Trp His Val His Thr Met Met Asn Val
            100                 105                 110

Gln Gly Gly Gly Pro Ile Ile Gly Pro Gly Lys Trp Ile Thr Val Glu
        115                 120                 125

Gly Ser Met Ser Glu Phe Arg Asn
    130                 135

<210> SEQ ID NO 21
<211> LENGTH: 37
<212> TYPE: PRT
<213> ORGANISM: Artificial sequence
<220> FEATURE:
<223> OTHER INFORMATION: Synthetic protein

<400> SEQUENCE: 21

Gly Ser Gly Gly Gly Ser Thr Ser Arg Asp His Met Val Leu His Glu
1               5                   10                  15

Tyr Val Asn Ala Ala Gly Ile Thr Gly Gly Gly Ser Ala Trp Ser His
            20                  25                  30

Pro Gln Phe Glu Lys
        35

<210> SEQ ID NO 22
<211> LENGTH: 380
<212> TYPE: PRT
<213> ORGANISM: Artificial sequence
<220> FEATURE:
<223> OTHER INFORMATION: Synthetic protein

<400> SEQUENCE: 22

Met Lys Ile Glu Glu Gly Lys Leu Val Ile Trp Ile Asn Gly Asp Lys
1               5                   10                  15

Gly Tyr Asn Gly Leu Gln Ser Gly Leu Leu Ala Glu Ile Thr Pro Asp
            20                  25                  30
```

-continued

```
Lys Ala Lys Asp Thr Gly Ile Lys Val Thr Val Glu His Pro Asp Lys
         35                   40                  45

Leu Glu Glu Lys Phe Pro Gln Val Ala Ala Thr Gly Asp Gly Pro Asp
     50                  55                  60

Ile Ile Phe Trp Ala His Asp Arg Phe Gly Gly Tyr Ala Gln Ser Gly
 65                  70                  75                  80

Leu Leu Ala Glu Ile Thr Pro Asp Lys Ala Phe Gln Asp Lys Leu Tyr
             85                   90                  95

Pro Phe Thr Trp Asp Ala Val Arg Tyr Asn Gly Lys Leu Ile Ala Tyr
                100                 105                 110

Pro Ile Ala Val Glu Ala Leu Ser Leu Ile Tyr Asn Lys Asp Leu Leu
                115                 120                 125

Pro Asn Pro Pro Lys Thr Trp Glu Glu Ile Pro Ala Leu Asp Lys Glu
            130                 135                 140

Leu Lys Ala Lys Gly Lys Ser Ala Leu Met Phe Asn Leu Gln Glu Pro
145                 150                 155                 160

Tyr Phe Thr Trp Pro Leu Ile Ala Ala Asp Gly Gly Tyr Ala Phe Lys
                165                 170                 175

Tyr Glu Asn Gly Lys Tyr Asp Ile Lys Asp Val Gly Val Asp Asn Ala
                180                 185                 190

Gly Ala Lys Ala Gly Leu Thr Phe Leu Val Asp Leu Ile Lys Asn Lys
            195                 200                 205

His Met Asn Ala Asp Thr Asp Tyr Ser Ile Ala Glu Ala Ala Phe Asn
        210                 215                 220

Lys Gly Glu Thr Ala Met Thr Ile Asn Gly Pro Trp Ala Trp Ser Asn
225                 230                 235                 240

Ile Asp Thr Ser Lys Val Asn Tyr Gly Val Thr Val Leu Pro Thr Phe
                245                 250                 255

Lys Gly Gln Pro Ser Lys Pro Phe Val Gly Val Leu Ser Ala Gly Ile
                260                 265                 270

Asn Ala Ala Ser Pro Asn Lys Glu Leu Ala Lys Glu Phe Leu Glu Asn
            275                 280                 285

Tyr Leu Leu Thr Asp Glu Gly Leu Glu Ala Val Asn Lys Asp Lys Pro
        290                 295                 300

Leu Gly Ala Val Ala Leu Lys Ser Tyr Glu Glu Leu Val Lys Asp
305                 310                 315                 320

Pro Arg Ile Ala Ala Thr Met Glu Asn Ala Gln Lys Gly Glu Ile Met
                325                 330                 335

Pro Asn Ile Pro Gln Met Ser Ala Phe Trp Tyr Ala Val Arg Thr Ala
            340                 345                 350

Val Ile Asn Ala Ala Ser Gly Arg Gln Thr Val Asp Glu Ala Leu Lys
        355                 360                 365

Asp Ala Gln Thr Asn Glu Asn Leu Tyr Phe Gln Gly
        370                 375                 380
```

<210> SEQ ID NO 23
<211> LENGTH: 402
<212> TYPE: PRT
<213> ORGANISM: Artificial sequence
<220> FEATURE:
<223> OTHER INFORMATION: Synthetic protein

```
<400> SEQUENCE: 23

His Gly Glu Lys Ser Gln Ala Ala Phe Met Arg Met Arg Thr Ile His
1               5                   10                  15

Trp Tyr Asp Leu Ser Trp Ser Lys Glu Lys Val Lys Ile Asn Glu Thr
            20                  25                  30

Val Glu Ile Lys Gly Lys Phe His Val Phe Glu Gly Trp Pro Glu Thr
        35                  40                  45

Val Asp Glu Pro Asp Val Ala Phe Leu Asn Val Gly Met Pro Gly Pro
    50                  55                  60

Val Phe Ile Arg Lys Glu Ser Tyr Ile Gly Gly Gln Leu Val Pro Arg
65                  70                  75                  80

Ser Val Arg Leu Glu Ile Gly Lys Thr Tyr Asp Phe Arg Val Val Leu
                85                  90                  95

Lys Ala Arg Arg Pro Gly Asp Trp His Val His Thr Met Met Asn Val
            100                 105                 110

Gln Gly Gly Gly Pro Ile Ile Gly Pro Gly Lys Trp Ile Thr Val Glu
        115                 120                 125

Gly Ser Met Ser Glu Phe Arg Asn Pro Val Thr Thr Leu Thr Gly Gln
    130                 135                 140

Thr Val Asp Leu Glu Asn Gly Glu Pro Ser Thr Tyr Lys Leu Ile Leu
145                 150                 155                 160

Asn Gly Lys Thr Leu Lys Gly Glu Thr Thr Thr Glu Ala Val Asp Ala
                165                 170                 175

Ala Thr Ala Glu Lys Val Phe Lys Gln Tyr Ala Asn Asp Asn Gly Val
            180                 185                 190

Asp Gly Glu Trp Thr Tyr Asp Asp Ala Thr Lys Thr Phe Thr Val Thr
        195                 200                 205

Glu Gly Glu Pro Val Glu Tyr Asn Gly Met Leu Met Ser Ile Ala Asp
    210                 215                 220

Ile Gln Gly Tyr Asn Tyr Val Arg Thr Gly Thr Pro Glu Tyr Ile Arg
225                 230                 235                 240

Met Val Glu Lys Gly Ser Gly Thr Met Arg Gly Met Lys Pro Leu Glu
                245                 250                 255

Leu Pro Ala Pro Thr Val Ser Val Lys Val Glu Asp Ala Thr Tyr Arg
            260                 265                 270

Val Pro Gly Arg Ala Met Arg Met Lys Leu Thr Ile Thr Asn His Gly
        275                 280                 285

Asn Ser Pro Ile Arg Leu Gly Glu Phe Tyr Thr Ala Ser Val Arg Phe
    290                 295                 300

Leu Asp Ser Asp Val Tyr Lys Asp Thr Thr Gly Tyr Pro Glu Asp Leu
305                 310                 315                 320

Leu Ala Glu Asp Gly Leu Ser Val Ser Asp Asn Ser Pro Leu Ala Pro
                325                 330                 335

Gly Glu Thr Arg Thr Val Asp Val Thr Ala Ser Asp Ala Ala Trp Glu
            340                 345                 350

Val Tyr Arg Leu Ser Asp Ile Ile Tyr Asp Pro Asp Ser Arg Phe Ala
        355                 360                 365

Gly Leu Leu Phe Phe Phe Asp Ala Thr Gly Asn Arg Gln Val Val Gln
    370                 375                 380

Ile Asp Ala Pro Leu Ile Pro Ser Phe Met Glu Asn Leu Tyr Phe Gln
385                 390                 395                 400

Gly Gly
```